United States Patent
Tully et al.

(10) Patent No.: US 8,771,935 B2
(45) Date of Patent: *Jul. 8, 2014

(54) SCREENING METHODS FOR COGNITIVE ENHANCERS

(75) Inventors: Timothy P Tully, Solana Beach, CA (US); Roderick E. M. Scott, New York, NY (US); Rusiko Bourtchouladze, New York, NY (US)

(73) Assignee: Dart Neuroscience (Cayman) Ltd., Camana Bay, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/364,504

(22) Filed: Feb. 2, 2012

(65) Prior Publication Data

US 2012/0171124 A1 Jul. 5, 2012

Related U.S. Application Data

(63) Continuation of application No. 10/527,950, filed as application No. PCT/US03/25942 on Aug. 19, 2003, now Pat. No. 8,124,330.

(60) Provisional application No. 60/404,620, filed on Aug. 19, 2002, provisional application No. 60/406,405, filed on Aug. 26, 2002.

(51) Int. Cl.

| C12Q 1/00 | (2006.01) |
| C12Q 1/66 | (2006.01) |
| C12Q 1/68 | (2006.01) |
| C12N 5/07 | (2010.01) |
| C12N 5/0793 | (2010.01) |

(52) U.S. Cl.
USPC .................. 435/4; 435/8; 435/6.13; 435/325; 435/368

(58) Field of Classification Search
None
See application file for complete search history.

(56) References Cited

U.S. PATENT DOCUMENTS 6,063,583 A 5/2000 Montminy

FOREIGN PATENT DOCUMENTS

| WO | 9611270 | 4/1996 |
| WO | 0213867 | 2/2002 |

OTHER PUBLICATIONS

Bevilaqua, et al., Behavioral Phamacology, Rapid Science, Publishers, vol. 8, No. 4, pp. 331-338 (1997).
Milner, et al., Neuron, 20:445-468 (1998).
Taubenfeld, et al., Journal of Neuriscience, vol. 21, No. 1, pp. 84-91 (2001).
Insel, et al., Cell Mol Neurobiol 23:305-314 (2003).
Tully, T. et al., Nature Rev Drug Discovery 2:267-276 (2003).
Sheriff, et al., Reg. Pept. 75-76:309-318 (1998).
Herzog, et al., PNAS 89:5794-5798 (1992).
Ji, et al., Neurobiol Dis 8:1-10 (2001).
Barad et al., PNAS 95:15020-15025 (1998).
Scott, Roderick et al., Journal of Molecular Neuroscience, vol. 19, No. 1-2 , pp. 171-177 (Aug. 2002).
Impey, S. et al., Nature Neuroscience, Nature America, Inc., US vol. 1, No. 7, 595-601 (Nov. 1998).
Shastry, et al., Intern J. Neurosc., 108, 109-126 (2001).
Walton, et al., Trends Neurosc., 23:48-53 (2000).
Torrance, et al., Nature Biotech 19:942-945 (2001).
Shoemaker et al., Can. Res. 45:2145-2153 (1985).
Ying et al., Journal of Biological Chemistry 272:2412-2420 )1997).

*Primary Examiner* — Daniel E Kolker
*Assistant Examiner* — Aditi Dutt
(74) *Attorney, Agent, or Firm* — Don J. Pelto, Esquire.; Sheppard, Mullin, Richter & Hampton LLP

(57) ABSTRACT

The present invention provides methods for identifying cognitive enhancers able to enhance CREB pathway function. Cognitive enhancers identified in accordance with the invention can be used in rehabilitating an animal with cognitive dysfunction and for enhancing memory or normal cognitive performance (ability or function) in the animal.

13 Claims, 2 Drawing Sheets

SEQUENCE LISTING

```
<160> NUMBER OF SEQ ID NOS: 48

<210> SEQ ID NO 1
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 1
cctccgccgc gtcactca                                               18

<210> SEQ ID NO 2
<211> LENGTH: 18
<212> TYPE: DNA
```

<213> ORGANISM: Artificial Sequence
<220> FEATURE:
<223> OTHER INFORMATION: LNA oligonucleotide

<400> SEQUENCE: 2
ccacgtaaca caccgcgt                                                18

<210> SEQ ID NO 3
<211> LENGTH: 20
<212> TYPE: DNA
<213> ORGANISM: Artificial Sequence
<220> FEATURE:
<223> OTHER INFORMATION: LNA oligonucleotide

<400> SEQUENCE: 3
tggtcattta gttaccggtg                                              20

<210> SEQ ID NO 4
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 4
gctggttgtc tgcaccag                                                18

<210> SEQ ID NO 5
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 5
ttttcagctt ctgttaca                                                18

<210> SEQ ID NO 6
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 6
ctgggcttga actgtcat                                                18

<210> SEQ ID NO 7
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 7
gctaatgtgg caatctgt                                                18

<210> SEQ ID NO 8
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 8
tgctggcatg gatacctg                                                18

<210> SEQ ID NO 9
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 9
gcagatgatg ttgcatga                                                 18

<210> SEQ ID NO 10
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 10
tgtctgccca ttgggcag                                                 18

<210> SEQ ID NO 11
<211> LENGTH: 19
<212> TYPE: DNA
<213> ORGANISM: Artificial Sequence
<220> FEATURE:
<223> OTHER INFORMATION: LNA oligonucleotide

<400> SEQUENCE: 11
gggccgcctg gataacgcc                                                19

<210> SEQ ID NO 12
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 12
ttcactttct gcaatagt                                                 18

<210> SEQ ID NO 13
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 13
tccacagact cctgtgaa                                                 18

<210> SEQ ID NO 14
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 14
aaaggatttc ccttcgtt                                                 18

<210> SEQ ID NO 15
<211> LENGTH: 18
<212> TYPE: DNA
<213> ORGANISM: Artificial Sequence
<220> FEATURE:

```
<223> OTHER INFORMATION: LNA oligonucleotide

<400> SEQUENCE: 15
cagaagataa gtcattca                                                   18

<210> SEQ ID NO 16
<211> LENGTH: 17
<212> TYPE: DNA
<213> ORGANISM: Artificial Sequence
<220> FEATURE:
<223> OTHER INFORMATION: LNA oligonucleotide

<400> SEQUENCE: 16
ttctcaatcc ttggcac                                                    17

<210> SEQ ID NO 17
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 17
tggcactgtt acagtggt                                                   18

<210> SEQ ID NO 18
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 18
ctgcccactg ctagtttg                                                   18

<210> SEQ ID NO 19
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 19
gctcctccgt cactgctt                                                   18

<210> SEQ ID NO 20
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 20
tgcactaagg ttacagtg                                                   18

<210> SEQ ID NO 21
<211> LENGTH: 42
<212> TYPE: DNA
<213> ORGANISM: Artificial Sequence
<220> FEATURE:
<223> OTHER INFORMATION: oligonucleotide probe

<400> SEQUENCE: 21
ggatttccct tcgttttkgg gtttttctct tggaaagaaa gt                         42
```

```
<210> SEQ ID NO 22
<211> LENGTH: 41
<212> TYPE: DNA
<213> ORGANISM: Artificial Sequence
<220> FEATURE:
<223> OTHER INFORMATION: oligonucleotide probe

<400> SEQUENCE: 22
caatccttgg cacccctggt tttttctctt ggaaagaaag t                          41

<210> SEQ ID NO 23
<211> LENGTH: 47
<212> TYPE: DNA
<213> ORGANISM: Artificial Sequence
<220> FEATURE:
<223> OTHER INFORMATION: oligonucleotide probe

<400> SEQUENCE: 23
agtctcctct tctgactttt cttcttttt tctcttggaa agaaagt                     47

<210> SEQ ID NO 24
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 24
tcctccctgg gtaatggcat ttttctcttg gaaagaaagt                            40

<210> SEQ ID NO 25
<211> LENGTH: 44
<212> TYPE: DNA
<213> ORGANISM: Artificial Sequence
<220> FEATURE:
<223> OTHER INFORMATION: oligonucleotide probe

<400> SEQUENCE: 25
ccattgttag ccagctgtat tgcttttct cttggaaaga aagt                        44

<210> SEQ ID NO 26
<211> LENGTH: 39
<212> TYPE: DNA
<213> ORGANISM: Artificial Sequence
<220> FEATURE:
<223> OTHER INFORMATION: oligonucleotide probe

<400> SEQUENCE: 26
ccggctgagt ggcagctgtt tttctcttgg aaagaaagt                             39

<210> SEQ ID NO 27
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 27
gcctgaggca gcttgaacat ttttctcttg gaaagaaagt                            40

<210> SEQ ID NO 28
<211> LENGTH: 41
<212> TYPE: DNA
<213> ORGANISM: Artificial Sequence
<220> FEATURE:
<223> OTHER INFORMATION: oligonucleotide probe
```

<400> SEQUENCE: 28
tgctgcttct tcagcaggct tttttctctt ggaaagaaag t          41

<210> SEQ ID NO 29
<211> LENGTH: 43
<212> TYPE: DNA
<213> ORGANISM: Artificial Sequence
<220> FEATURE:
<223> OTHER INFORMATION: oligonucleotide probe

<400> SEQUENCE: 29
ttagacggac ctctctcttc cgttttctc ttggaaagaa agt          43

<210> SEQ ID NO 30
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 30
gaatcttcac tttctgcaat agttgatttt taggcatagg acccgtgtct          50

<210> SEQ ID NO 31
<211> LENGTH: 53
<212> TYPE: DNA
<213> ORGANISM: Artificial Sequence
<220> FEATURE:
<223> OTHER INFORMATION: oligonucleotide probe

<400> SEQUENCE: 31
aatcagttac actatccaca gactcctgtt ttttaggcat aggacccgtg tct          53

<210> SEQ ID NO 32
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 32
atgtactgcc cactgctagt ttggtatttt taggcatagg acccgtgtct          50

<210> SEQ ID NO 33
<211> LENGTH: 44
<212> TYPE: DNA
<213> ORGANISM: Artificial Sequence
<220> FEATURE:
<223> OTHER INFORMATION: oligonucleotide probe

<400> SEQUENCE: 33
ggccctgtac cccatccgta tttttaggca taggacccgt gtct          44

<210> SEQ ID NO 34
<211> LENGTH: 48
<212> TYPE: DNA
<213> ORGANISM: Artificial Sequence
<220> FEATURE:
<223> OTHER INFORMATION: oligonucleotide probe

<400> SEQUENCE: 34
cattggtcat ggttaatgtc tgcattttta ggcataggac ccgtgtct          48

<210> SEQ ID NO 35
<211> LENGTH: 52

```
<212> TYPE: DNA
<213> ORGANISM: Artificial Sequence
<220> FEATURE:
<223> OTHER INFORMATION: oligonucleotide probe

<400> SEQUENCE: 35
gtctgtgcat actgtagaat ggtagtactt tttaggcata ggacccgtgt ct        52

<210> SEQ ID NO 36
<211> LENGTH: 45
<212> TYPE: DNA
<213> ORGANISM: Artificial Sequence
<220> FEATURE:
<223> OTHER INFORMATION: oligonucleotide probe

<400> SEQUENCE: 36
agaatctgct gtccatccgt gtttttaggc ataggacccg tgtct              45

<210> SEQ ID NO 37
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 37
gtgcgaatct ggtatgtttg tacatctttt taggcatagg acccgtgtct         50

<210> SEQ ID NO 38
<211> LENGTH: 44
<212> TYPE: DNA
<213> ORGANISM: Artificial Sequence
<220> FEATURE:
<223> OTHER INFORMATION: oligonucleotide probe

<400> SEQUENCE: 38
acgccataac aactccaggg tttttaggca taggacccgt gtct               44

<210> SEQ ID NO 39
<211> LENGTH: 23
<212> TYPE: DNA
<213> ORGANISM: Artificial Sequence
<220> FEATURE:
<223> OTHER INFORMATION: oligonucleotide probe

<400> SEQUENCE: 39
cctgtaggaa ggcctccttg aaa                                      23

<210> SEQ ID NO 40
<211> LENGTH: 29
<212> TYPE: DNA
<213> ORGANISM: Artificial Sequence
<220> FEATURE:
<223> OTHER INFORMATION: oligonucleotide probe

<400> SEQUENCE: 40
gcatcagaag ataagtcatt caaaatttt                                29

<210> SEQ ID NO 41
<211> LENGTH: 19
<212> TYPE: DNA
<213> ORGANISM: Artificial Sequence
<220> FEATURE:
<223> OTHER INFORMATION: oligonucleotide probe

<400> SEQUENCE: 41
```
tggtgatggc aggggctga                    19

<210> SEQ ID NO 42
<211> LENGTH: 23
<212> TYPE: DNA
<213> ORGANISM: Artificial Sequence
<220> FEATURE:
<223> OTHER INFORMATION: oligonucleotide probe

<400> SEQUENCE: 42 aatggggtt ggcactgtta cag                    23

<210> SEQ ID NO 43
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 43
acaacttggt tgctgggcac t                    21

<210> SEQ ID NO 44
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 44
gcaatggtgc tagtgggtgc t                    21

<210> SEQ ID NO 45
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 45
gtgtaggaag tgctggggag g                    21

<210> SEQ ID NO 46
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 46
cctccgccgc gtcactca                    18

<210> SEQ ID NO 47
<211> LENGTH: 18
<212> TYPE: DNA
<213> ORGANISM: Artificial Sequence
<220> FEATURE:
<223> OTHER INFORMATION: LNA oligonucleotide

<400> SEQUENCE: 47
ccacgtaaca caccgcgt                    18

<210> SEQ ID NO 48
<211> LENGTH: 18
<212> TYPE: DNA
<213> ORGANISM: Artificial Sequence

```
<220> FEATURE:
<223> OTHER INFORMATION: LNA oligonucleotide

<400> SEQUENCE: 48
tggcactgtt acagtggt                                                  18
```

SCREENING METHODS FOR COGNITIVE ENHANCERS

RELATED APPLICATIONS

This application is a continuation of U.S. application Ser. No. 10/527,950, filed Sep. 30, 2005, now U.S. Pat. No. 8,124,330, which is the U.S. National Stage of International Application No. PCT/US2003/025942, filed 19 Aug. 2003, published in English, which claims the benefit of U.S. Provisional Application No. 60/404,620, filed 19 Aug. 2002, and U.S. Provisional Application No. 60/406,405, filed 26 Aug. 2002. The entire teachings of these applications are incorporated herein by reference.

BACKGROUND OF THE INVENTION

An estimated 4 to 5 million Americans (about 2% of all ages and 15% of those older than age 65) have some form and degree of cognitive failure. Cognitive failure (dysfunction or loss of cognitive functions, the process by which knowledge is acquired, retained and used) commonly occurs in association with central nervous system (CNS) disorders or conditions, including age-associated memory impairment, delirium (sometimes called acute confusional state), dementia (sometimes classified as Alzheimer's or non-Alzheimer's type), Alzheimer's disease, Parkinson's disease, Huntington's disease (chorea), cerebrovascular disease (e.g., stroke, ischemia), affective disorders (e.g., depression), psychotic disorders (e.g., schizophrenia, autism (Kanner's Syndrome)), neurotic disorders (e.g., anxiety, obsessive-compulsive disorder), attention deficit disorder (ADD), subdural hematoma, normal-pressure hydrocephalus, brain tumor, head or brain trauma.

Cognitive dysfunction is typically manifested by one or more cognitive deficits, which include memory impairment (impaired ability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (i.e., planning, organizing, sequencing, abstracting).

Cognitive dysfunction causes significant impairment of social and/or occupational functioning, which can interfere with the ability of an individual to perform activities of daily living and greatly impact the autonomy and quality of life of the individual. Thus, there is considerable interest in identifying clinical candidates for use in rehabilitating an animal with any form of cognitive dysfunction.

SUMMARY OF THE INVENTION

The present invention relates to high throughput cell-based methods (assays) to identify or screen for cognitive enhancers that act by increasing CREB pathway function. The invention enables the identification of cognitive enhancers that have little to no effect on CREB pathway function alone, but act to increase (enhance) CREB pathway function in combination with a CREB function stimulating agent. Cognitive enhancers identified in accordance with the invention are expected to yield effective clinical candidates for use in rehabilitating an animal with cognitive dysfunctions and for use in enhancing memory or normal cognitive performance (ability or function) in a normal animal. "Cognitive enhancers" are also referred to herein as "compounds able to enhance CREB pathway function" and "CREB pathway enhancing drugs". "CREB function stimulating agents" are also referred to herein as "agents that stimulate CREB pathway function". It is understood that, in certain instances, a cognitive enhancer identified in accordance with the present invention can be a CREB function stimulating agent. Thus, a CREB function stimulating agent may be identified as a cognitive enhancer using the methods described herein.

As described herein, methods for identifying or screening for cognitive enhancers comprise a primary screen, a secondary screen and a tertiary screen. Preferably, the primary screen is a cell-based method used to identify candidate compounds; the secondary screen is a cell-based method used to identify confirmed candidate compounds; and the tertiary screen uses a behavior model to identify cognitive enhancers.

The primary screen comprises: (a) contacting host cells (particularly cells of neural origin (e.g., neuroblastomas, neural stem cells)) comprising an indicator gene operably linked to a CRE promoter with a test compound and with a suboptimal dose of a CREB function stimulating agent (e.g., forskolin); (b) determining indicator activity in host cells which have been contacted with the test compound and with the CREB function stimulating agent, (c) comparing the indicator activity determined in step (b) with the indicator activity in control cells which have been contacted with the CREB function stimulating agent and which have not been contacted with the test compound (i.e., control cells which have been contacted with the CREB function stimulating agent alone); (d) selecting the test compound If (1) the indicator activity determined in step (b) is statistically significantly increased relative to the indicator activity in the control cells of step (c); and (2) the indicator activity in control cells which have not been contacted with the CREB function stimulating agent and which have been contacted with the test compound (i.e., control cells which have been contacted with test compound alone) is not statistically significantly different relative to the indicator activity in control cells which have not been contacted with either the CREB function stimulating agent or the test compound (i.e., control cells which have been contacted with nothing); (e) repeating steps (a) to (d) with a range of different concentrations (e.g., 2 or more) of the test compound selected in step (d); and (f) selecting the test compound if: (1) the indicator activity is proportionally statistically significantly increased in the range of different concentrations for said test compound relative to the indicator activity in the control cells which have been contacted with the CREB function stimulating agent alone; and (2) the indicator activity in control cells to which have been introduced the range of different concentrations of the test compound alone is not significantly different relative to the indicator activity in control cells which have not been contacted with either the CREB function stimulating agent or the test compound, wherein the test compound is identified as a candidate compound. In a particular embodiment, host cells are contacted with the test compound prior to contact with the CREB function stimulating agent. In another embodiment, the indicator gene encodes luciferase. An indicator gene operably linked to a CRE promoter is also referred to herein as a CRE-mediated indicator gene. A CRE-mediated indicator gene is an example of a CRE-mediated transgene.

Alternatively, the primary screen comprises: (a) contacting host cells (particularly cells of neural origin (e.g., neuroblastomas, neural stem cells)) with a test compound and with a suboptimal dose of a CREB function stimulating agent (e.g., forskolin); (b) assessing endogenous CREB-dependent gene expression in the host cells which have been contacted with the test compound and with the CREB function stimulating agent; (c) comparing endogenous CREB-dependent gene expression assessed in step (b) with endogenous CREB-dependent gene expression in control cells which have been contacted with the CREB function stimulating agent and which have not been contacted with the test compound (i.e., control cells which have been contacted with the CREB function stimulating agent alone); (d) selecting the test compound if (1) the endogenous CREB-dependent gene expression determined in step (b) is statistically significantly increased relative to the endogenous CREB-dependent gene expression in the control cells of step (c); and (2) the CREB-dependent gene expression in control cells to which have not been contacted with the CREB function stimulating agent and which have been contacted with the test compound (i.e., control cells which have been contacted with test compound alone) is not statistically significantly different relative to the CREB-dependent gene expression in control cells which have not been contacted with either the CREB function stimulating agent or the test compound (i.e., control cells which have been contacted with nothing); (e) repeating steps (a) to (d) with a range of different concentrations (e.g., 2 or more) of the test compound selected in step (d); and (f selecting the test compound if: (1) the CREB-dependent gene expression is proportionally statistically significantly increased in the range of different concentrations for said test compound relative to the CREB-dependent gene expression in the control cells which have been contacted with the CREB function stimulating agent alone; and (2) the CREB-dependent gene expression in control cells to which have been introduced the range of different concentrations of the test compound alone is not significantly different relative to the CREB-dependent gene expression in control cells which have not been contacted with either the CREB function stimulating agent or the test compound, wherein the test compound is identified as a candidate compound. In a particular embodiment, host cells are contacted with the test compound prior to contact with the CREB function stimulating agent.

The secondary screen comprises: (a) contacting cells of neural origin (particularly primary neurons (e.g., primary hippocampal cells)) with a candidate compound identified in the primary screen and with a suboptimal dose of a CREB function stimulating agent; (b) assessing endogenous CREB-dependent gene expression in the cells which have been contacted with the candidate compound and with the CREB function stimulating agent; and (c) comparing endogenous CREB-dependent gene expression assessed in step (b) with endogenous CREB-dependent gene expression in control cells which have been contacted with the CREB function stimulating agent and which have not been contacted with the candidate compound (i.e., control cells which have been contacted with CREB function stimulating agent alone). A statistically significant difference in CREB-dependent gene expression assessed in step (b) compared to the CREB-dependent gene expression in control cells which have been contacted with CREB function stimulating agent alone and no significant difference in CREB-dependent gene expression in control cells which have not been contacted with the CREB function stimulating agent and which have been contacted with the candidate compound (i.e., control cells contacted with candidate compound alone) relative to CREB-dependent gene expression in control cells which have not been contacted with either the CREB function stimulating agent or the candidate compound (i.e., control cells contacted with nothing) identifies the candidate compound as a confirmed candidate compound. In a particular embodiment, cells are contacted with the candidate compound prior to contact with the CREB function stimulating agent.

Alternatively, the secondary screen comprises: (a) contacting cells of neural origin particularly primary neurons (e.g., primary hippocampal cells)) comprising an indicator gene operably linked to a CRE promoter with a candidate compound identified in the primary screen and with a suboptimal dose of a CREB function stimulating agent; (b) determining indicator activity in the cells which have been contacted with the candidate compound and with the CREB function stimulating agent; and (c) comparing indicator activity assessed in step (b) with indicator activity in control cells which have been contacted with the CREB function stimulating agent and which have not been contacted with the candidate compound (i.e., control cells which have been contacted with CREB function stimulating agent alone). A statistically significant difference in indicator activity determined in step (b) compared to the indicator activity in control cells which have been contacted with CREB function stimulating agent alone and no significant difference in indicator activity in control cells which have been contacted with the CREB function stimulating agent and which have not been contacted with the candidate compound (i.e., control cells contacted with candidate compound alone) relative to indicator activity in control cells which have not been contacted with either the CREB function stimulating agent or the candidate compound (i.e., control cells contacted with nothing) identifies the candidate compound as a confirmed candidate compound. In a particular embodiment, cells are contacted with the candidate compound prior to contact with the CREB function stimulating agent.

In a particular embodiment, the cells of neural origin used in the secondary screen are different from the host cells used in the primary screen. In another embodiment, the endogenous CRE-mediated gene or the CRE-mediated transgene in the secondary screen is different from the CRE-mediated transgene or the endogenous CRE-mediated gene in the primary screen. For example, in one embodiment the host cells in the primary screen are neuroblastomas and the cells in the secondary screen are not neuroblastomas. In another embodiment, the CRE-mediated transgene in the primary screen is luciferase (CRE operably linked to the luciferase gene) and the CRE-mediated transgene in the secondary screen is not luciferase. In a particular embodiment, the host cells in the primary screen are proliferating cells (such as neuroblastomas and neural stem cells) and the cells in the secondary screen are nonproliferating, differentiated cells of neural origin (such as neurons or glial cells). In another particular embodiment, the CRE-mediated gene in the primary screen is a CRE-mediated indicator gene (a CRE-mediated transgene) and the CRE-mediated gene in the secondary screen is an endogenous CRE-mediated gene.

In one embodiment, the tertiary screen is a behavioral method for assessing long term memory formation in an animal comprising: (a) administering an effective amount of a confirmed candidate compound identified in the secondary screen to the animal (e.g., human, other mammal, vertebrate or invertebrate); (b) training the animal administered the confirmed candidate compound under conditions appropriate to produce long term memory formation in the animal; (c) assessing long term memory formation in the animal trained in step (b); and (d) comparing long term memory formation assessed in step (c) with long term memory formation produced in the control animal to which the confirmed candidate compound has not been administered If an enhancement is noted in long term memory formation assessed in the animal treated with the confirmed candidate compound relative to the long term memory formation assessed in the control animal, the confirmed candidate compound is identified as a cognitive enhancer. Tertiary screens with very similar protocols are available using behavioral methods (models) for other cognitive dysfunctions.

The invention also relates to methods for assessing the effect of a compound on CREB-dependent gene expression (CRE-mediated gene expression) comprising: (a) contacting cells of neural origin particularly primary neurons (e.g., primary hippocampal cells) with a compound to be assessed and with a suboptimal dose of a CREB function stimulating agent; (b) assessing endogenous CREB-dependent gene expression in the cells which have been contacted with the compound and with the CREB function stimulating agent; and (c) comparing endogenous CREB-dependent gene expression assessed in step (b) with endogenous CREB-dependent gene expression in control cells which have been contacted with the CREB function stimulating agent and which have not been contacted with the compound (i.e., control cells which have been contacted with CREB function stimulating agent alone). A statistically significant difference in CREB-dependent gene expression assessed in step (b) compared to the CREB-dependent gene expression in control cells which have been contacted with CREB function stimulating agent alone and no significant difference in CREB-dependent gene expression in control cells which have not been contacted with the CREB function stimulating agent and which have been contacted with the compound (i.e., control cells contacted with compound alone) relative to CREB-dependent gene expression in control cells which have not been contacted with either CREB function stimulating agent or the compound (i.e., control cells contacted with nothing) identifies the compound as one having an effect on CREB-dependent gene expression. In a particular embodiment, cells are contacted with the compound to be assessed prior to contact with the CREB function stimulating agent. Preferably, the compound to be assessed is a candidate compound identified in the primary screen.

Alternatively, methods for assessing the effect of a compound on CREB-dependent gene expression comprise: (a) contacting cells of neural origin (particularly primary neurons (e.g., primary hippocampal cells) comprising an indicator gene operably linked to a CRE promoter with a compound to be assessed and with a suboptimal dose of a CREB function stimulating agent; (b) determining indicator activity in the cells which have been contacted with the compound and with the CREB function stimulating agent; and (c) comparing indicator activity determined in step (b) with indicator activity in control cells which have been contacted with the CREB function stimulating agent and which have not been contacted with the compound (i.e., control cells which have been contacted with CREB function stimulating agent alone). A statistically significant difference in indicator activity determined in step (b) compared to the indicator activity in control cells which have been contacted with CREB function stimulating agent alone and no significant difference in indicator activity in control cells which have not been contacted with the CREB function stimulating agent and which have been contacted with the compound (i.e., control cells contacted with compound alone) relative to indicator activity in control cells which have not been contacted with either CREB function stimulating agent or the compound (i.e., control cells contacted with nothing) identifies the compound as one having an effect on CREB-dependent gene expression. In a particular embodiment, cells are contacted with the compound to be assessed prior to contact with the CREB function stimulating agent. Preferably, the compound to be assessed is a candidate compound identified in the primary screen.

In a particular embodiment, the cells used in the methods for assessing the effect of a compound on CREB-dependent gene expression are different feom the host cells in the primary screen. In another embodiment, the endogenous CRE-mediated gene or the CRE-mediated transgene used in the methods for assessing the effect of a compound on CREB-dependent gene expression are different from the CRE-mediated transgene or the endogenous CRE-mediated gene in the primary screen.

The invention further relates to methods for assessing the effect of a cognitive enhancer on long term memory formation in an animal comprising: (a) administering an effective amount of cognitive enhancer to an animal (e.g., human, other mammal, vertebrate or invertebrate); (b) training the animal administered the cognitive enhancer under conditions appropriate to produce long term memory formation in the animal; (c) assessing long term memory formation in the animal trained in step Ado), and (d) comparing long term memory formation assessed in step (c) with long term memory formation produced in the control animal to which the cognitive enhancer has not been administered. If a difference is noted in long term memory formation assessed in the animal treated with the cognitive enhancer relative to the long term memory formation assessed in the control animal, the cognitive enhancer can be categorized as enhancing (improving, increasing) long term memory formation in the animal.

Cognitive enhancers identified in accordance with the invention can be used to reduce the duration and/or number of training sessions required for the induction in a specific neuronal circuit(s) of a pattern of neuronal activity or to reduce the duration and/or number of training sessions required to induce CREB-dependent long term structural/function (i.e., long-lasting) change among synaptic connections of the neuronal circuit. Cognitive enhancers identified in accordance with the invention can be used to reduce the number of training sessions required to induce a performance gain relative to that obtained with training alone or to enable shorter or no rest intervals between training sessions to induce a performance gain or to increase the overall level of performance.

DETAILED DESCRIPTION OF THE INVENTION

Figure 1:
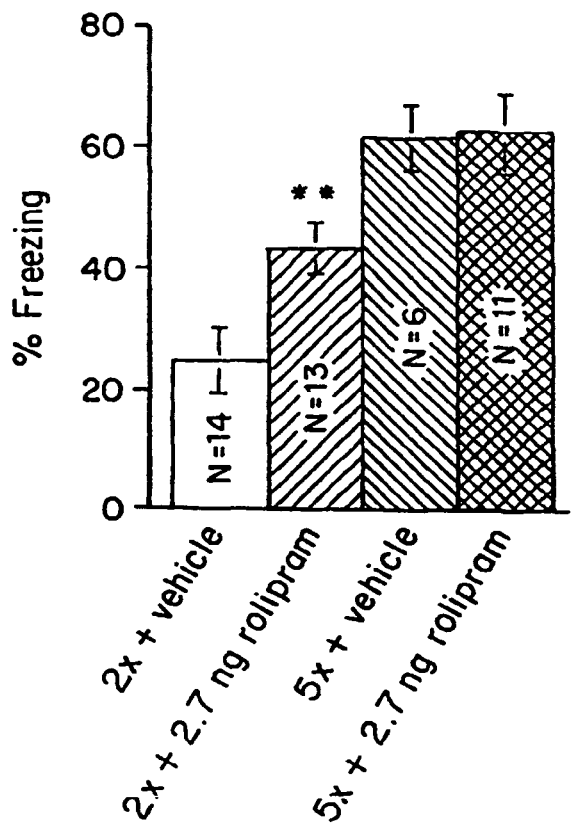
FIG. 1 is a bar graph showing the results of drug-induced (partial) enhancement of memory in normal mice by rolipram, a prototypical phosphodiesterase (PDE) inhibitor. Five-day retention after weak training (2×) is lower than strong training (5×). Only memory after weak training is enhanced by bilateral hippocampal injections (1 µl) of rolipram immediately after training. Rolipram reduced the number of training sessions required to produce memory. % Freezing=% Observation time mice spent frozen/motionless.
Figure 2:
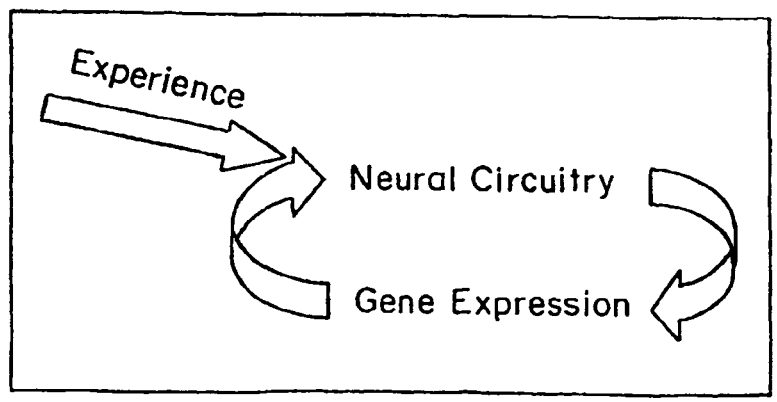
FIG. 2 is a schematic diagram showing that experience-dependent changes in neural activity modulate gene expression. Some of these changes in gene expression yield structural and functional changes in the synaptic connections among neurons. In this manner, neural circuitry is constantly fine-tuned to optimize perception cognition and behavioral responses.

The CREB transcription factor plays a primary role in the formation of long-term memory and the underlying long-term synaptic plasticity. Behavior-genetic studies of Pavlovian olfactory learning in *Drosophila* have established CREB to be a central switch for the conversion of newly acquired information from short-term memory to long-term memory (Tully, T. et al., Proc. Natl. Acad. Sci. USA, 94(9):4239-4241 (1997)). Spaced training after a Pavlovian odor-shock association task induces a protein synthesis-dependent long-term memory (Tully, T. et al., Cell, 79(1):35-47 (1994)), the formation of which is specifically blocked by induced expression of a CREB repressor transgene (Yin, J. C. et al., Cell, 79(1):49-58 (1994)). Learning and short-term (earlier) memory are normal in these transgenic flies (Tully, T. et al., Cell, 79(1):35-47 (1994); and Yin, J. C. et al., Cell, 79(1):49-58 (1994)). In contrast to these loss-of-function results, induced expression of a CREB activator transgene enhances long-term memory specifically by abrogating the requirements for repetitive training sessions and for a rest interval between each session (Yin, J. C. et al., Cell, 81(1):107-115 (1995)). One training session is sufficient to form maximal long-term memory in transgenic flies overexpressing CREB activator (Yin, J. C. et al., Cell, 81(1):107-115 (1995)). More long-term memory is not produced. Rather, long-term memory is induced with less practice.

This memory enhancement also is specific to the temporal association of two stimuli. High levels of CREB activator were induced in all cells of the fly due to the use of a heat-shock promoter with the transgene. In the absence of training, no measurable effect on the flies' behavior was observed. Moreover, spaced presentations of odor and shock, unpaired in time, failed to produce long-term memory in CREB-activator flies (flies induced to express high levels of CREB activator). These results suggest that associative learning induces the upstream signaling required to activate (phosphorylate) the CREB switch during olfactory long-term memory formation.

A growing body of evidence extends these results from invertebrates to mammals. For example, in Aplysia, molecular manipulations of CREB expression, similar to those in flies, suppress or enhance (1) long-term memory of a facilitatory electrophysiological response at a sensorimotor monosynapse in cell culture and (2) the synaptic connections between sensory and motor neurons that are normally produced after spaced applications of the facilitatory stimulus (Bartsch, D. et al., Cell, 83(6):979-992 (1995)). In a study focused on a form of traumatic memory, referred to as fear conditioning (Bourtchuladze, R P et al., Cell, 79(1):59-68 (1994)), mutant mice carrying a partial knock-out of CREB showed normal learning and short-term memory but long-term memory was abolished. In contrast, normal mice required only one training trial to form a long-term memory of this experience. These results suggest that (1) for the fear conditioning experiment, normal mice formed long-term memory more like the CREB-activator flies and (2) the CREB mutation in mice was partial, reducing the amount of activator isoform(s) relative to repressor isoform(s). This indicated that CREB mutant mice may have a functional CREB switch that is set to a level similar to that in normal flies. As such, spaced training would rescue the long-term memory deficit in CREB mutant mice. In fact, Kogan et al. showed that long-term memory can form normally in CREB mutant mice subjected to spaced, but not massed, training, thereby providing strong support for the CREB switch model (Kogan, J. H. et al., Curr. Biol., 7(1):1-1 (1997)).

In rats, injections of antisense RNA oligonucleotides into hippocampus or amygdala block long-term memory formation of two different tasks that are dependent on activity in these anatomical regions, respectively (Guzowski, J. F. and McGaugh, J. L., Proc. Natl. Acad. Sci. USA, 94(6):2693-2698 (1997); and Lamprecht, R. et al., J. Neurosci., 17(21): 8443-8450 (1997)). In particular, the RNA antisense experiments revealed a role for CREB during long-term memory formation of a water-maze task (hippocampal-dependent) and conditioned taste aversion (amygdala-dependent) in rats (Guzowski, J. F. and McGaugh, J. L., Proc. Natl. Acad. Sci. USA, 94(6):2693-2696 (1997); and Lamprecht, R. et al., J. Neurosci., 17(21):8443-8450 (1997)).

More recent experiments have over expressed CREB activator in the amygdala and observed enhanced memory formation of a fear-potentiated startle response in rats, with a CREB signature similar to that observed in flies (Josselyn, S. A. et al., Society for Neuroscience, 28th Annual Meeting, Vol. 24, Abstract 365.10 (1998); and Josselyn, S. A. et al., J. Neurosci., 21(7):2404-2412 (2001)).

Cellular observations in mice and rats have reinforced these behavioral results by revealing that neuronal CREB function (phosphorylation or gene-regulation) is modulated in an experience-dependent fashion (Impey, S. et al., Neuron, 16(5):973-982 (1996); Taubenfeld S. M. et al., Nat. Neurosci., 2(4):309-310 (1999); and Taubenfeld, S. M. et al., J. Neurosci., 21(1):84-91 (2001)).

In addition to being involved in the formation of experiential memories, CREB also appears to function in the developmental and cellular plasticity of several cortical regions (Ahn, S. et al., Neuron, 23(3):559-568 (1999); Barth, A. L. et al., J. Neurosci., 20(10:4206-4216 (2000); Glazewski, S. et al., Cerebral Cortex, 9(3):249-256 (1999); Pham, T. A. et al., Neuron, 22(1):63-72 (1999); and Pham, T. A. et al., Neuron, 31(3):409-420 (2001)). Neuronal activity increases CREB activity in cortex (Moore, A. N. et al., J. Biol. Chem., 271 (24):14214-14220 (1996)). CREB also mediates developmental plasticity in hippocampus (Murphy, D. D. and Segal, M., Proc. Natl. Acad. Sci. USA, 94(4):1482-1487 (1997)), in somatosensory cortex (Glazewski, S. et al., Cerebral Cortex, 9(3):249-256 (1999)), in striatum (Liu, F. C. and Graybiel, A. M., Neuron, 17(6):1133-1144 (1996)) and in visual cortex (Pham, T. A. et al, Neuron, 22(1):63-72 (1999)). These data support the idea that CREB is a molecular switch generally involved in converting neural activity to structural changes at synapses. As such, the CREB pathway represents (1) a significant target for new drug discovery and (2) a genetic beachhead for the identification of downstream genes that also participate in activity-dependent synaptic plasticity.

The present invention provides methods to identify or screen for these drugs, also referred to herein as cognitive enhancers. The invention provides high throughput cell-based methods (assays) to identify or screen for cognitive enhancers that act by increasing CREB pathway function.

Cognitive enhancers can increase, enhance or improve CREB pathway function by a variety of mechanisms. For example, a cognitive enhancer can affect a signal transduction pathway which leads to induction of CREB-dependent gene expression. Induction of CREB-dependent gene expression can be achieved, for example, via up-regulation of positive effectors of CREB function and/or down-regulation of negative effectors of CREB function. Positive effectors of CREB function include adenylate cyclases and CREB activators. Negative effectors of CREB function include cAMP phosphodiesterase (cAMP PDE) and CREB repressors.

A cognitive enhancer can increase, enhance or improve CREB pathway function by acting biochemically upstream of or directly acting on an activator or repressor form of a CREB protein and/or on a CREB protein containing transcription complex. For example, CREB pathway function can be affected by increasing CREB protein levels transcriptionally, post-transcriptionally, or both transcriptionally and post-transcriptionally, by altering the affinity of CREB protein to other necessary components of the of the transcription complex, such as, for example, to CREB-binding protein (CBP protein); by altering the affinity of a CREB protein containing transcription complex for DNA CREB responsive elements in the promoter region; or by inducing either passive or active immunity to CREB protein isoforms. The particular mechanism by which a cognitive enhancer increases, enhances or improves CREB pathway function is not critical to the practice of the invention.

By "increase CREB pathway function" or "enhance CREB pathway function" is meant the ability to increase, enhance or improve CREB-dependent gene expression. By "modulate CREB pathway function" is meant the ability to modulate CREB-dependent gene expression. CREB-dependent gene expression can be increased, enhanced or improved by increasing endogenous CREB production, for example by directly or indirectly stimulating the endogenous gene to produce increased amounts of CREB, or by increasing functional (biologically active) CREB. See, e.g., U.S. Pat. No. 5,929,223; U.S. Pat. No. 6,051,559; and International Publication No. WO96/11270 (published Apr. 18, 1996), which references are incorporated herein in their entirety by reference. By "increasing functional (biologically active) CREB" is meant to include the ability to increase DNA binding ability, phosphorylation state, protein stability, subcellular localization, etc. CREB-dependent gene expression can be modulated by increasing or decreasing endogenous CREB production, for example by directly or indirectly stimulating the endogenous gene to produce increased or decreased amounts of CREB, or by increasing or decreasing functional (biologically active) CREB.

As described herein, methods for identifying or screening for cognitive enhancers comprise a primary screen, a secondary screen and a tertiary screen. Preferably, the primary screen is a cell-based method used to identify candidate compounds; the secondary screen is a cell-based method used to identify confirmed candidate compounds; and the tertiary screen uses a behavior model to identify cognitive enhancers. Primary and secondary screens include high throughput cell-based methods.

The primary screen comprises: (a) contacting host cells comprising an indicator gene operably linked to a CRE promoter with a test compound and with a suboptimal dose of a stimulating agent that activates signaling pathways onto CREB; (b) determining indicator activity in host cells which have been contacted with the test compound and with the stimulating agent; (c) comparing the indicator activity determined in step (b) with the indicator activity in control cells which have been contacted with the stimulating agent and which have not been contacted with the test compound (control cells which have been contacted with stimulating agent alone); (d) selecting the test compound if (1) the indicator activity determined in step (b) is statistically significantly increased relative to the indicator activity in the control cells of step (c); and (2) the indicator activity in control cells which have not been contacted with the stimulating agent and which have been contacted with the test compound (control cells contacted with test compound alone) is not statistically significantly different relative to the indicator activity in control cells which have been contacted with neither the stimulating agent or the test compound (controls cells which have been contacted with nothing); (e) repeating steps (a) to (d) with a range of different concentrations of the test compound selected in step (d); and (f) selecting the test compound if: (1) the indicator activity is proportionally statistically significantly increased in the range of different concentrations of said test compound relative to the indicator activity in the control cells to which have been contacted with the stimulating agent alone; and (2) the indicator activity in control cells to which have been introduced the range of different concentrations of the test compound alone is not significantly different relative to the indicator activity in control cells which have not been contacted with either the stimulating agent or the test compound, wherein the test compound is identified as a candidate compound. In a particular embodiment, the test compound is selected in step (f) if (1) the indicator activity is proportionally significantly increased in the linear range of different concentrations for the test compound; and (2) the indicator activity in control cells to which have been introduced the range of different concentrations of the test compound alone is not significantly different relative to the indicator activity in control cells which have not been contacted with either the stimulating agent or the test compound. In another embodiment, host cells are contacted with the test compound prior to contact with the stimulating agent.

Alternatively, the primary screen comprises: (a) contacting host cells with a test compound and with a suboptimal dose of a stimulating agent that activates signaling pathways onto CREB; (b) assessing endogenous CREB-dependent gene expression in the host cells which have been contacted with the test compound and with the stimulating agent; (c) comparing endogenous CREB-dependent gene expression assessed in step (b) with endogenous CREB-dependent gene expression in control cells which have been contacted with the stimulating agent and which have not been contacted with the test compound (control cells which have been contacted with stimulating agent alone); (d) selecting the test compound if (1) the endogenous CREB-dependent gene expression determined in step (b) is statistically significantly increased relative to the endogenous CREB-dependent gene expression in the control cells of step (c); and (2) the CREB-dependent gene expression in control cells which have not been contacted with the stimulating agent and which have been contacted with the test compound (control cells which have been contacted with test compound alone) is not statistically significantly different relative to the CREB-dependent gene expression in control cells which have been contacted with neither the stimulating agent or the test compound (controls cells which have been contacted with nothing); (e) repeating steps (a) to (d) with a range of different concentrations of the test compound selected in step (d); and (f) selecting the test compound if: (1) the CREB-dependent gene expression is proportionally statistically significantly increased in the range of different concentrations for said test compound relative to the CREB-dependent gene expression in the control cells which have been contacted with the stimulating agent alone; and (2) the CREB-dependent gene expression in control cells to which have been introduced the range of different concentrations of the test compound alone is not significantly different relative to the CREB-dependent gene expression in control cells which have been contacted with neither the stimulating agent or the test compound, wherein the test compound is identified as a candidate compound. In a particular embodiment, the test compound is selected in step (f) if (1) the CREB-dependent gene expression is proportionally significantly increased in the linear range of the different concentrations for the test compound; and (2) the CREB-dependent gene expression in control cells to which have been introduced the range of different concentrations of the test compound alone is not significantly different relative to the CREB-dependent gene expression in control cells which have not been contacted with either the stimulating agent or the test compound. In another embodiment, host cells are contacted with the test compound prior to contact with the stimulating agent.

Preferably, the "stimulating agent that activates signaling pathways onto CREB" used in the primary screen is a CREB function stimulating agent. A CREB function stimulating agent is an agent that is able to stimulates CREB pathway function. By "stimulate CREB pathway function" is meant the ability to stimulate CREB-dependent gene expression by stimulating endogenous CREB production, for example by directly or indirectly stimulating the endogenous gene to produce increased amounts of CREB, or by increasing functional (biologically active) CREB. See, e.g., U.S. Pat. No. 5,929,223); U.S. Pat. No. 6,051,559; and International Publication No. WO96/11270 (published Apr. 18, 1996), which references are incorporated herein in their entirety by reference. "CREB function stimulating agents" include drugs, chemical compounds, ionic compounds, organic compounds, organic ligands, including cofactors, saccharides, recombinant and synthetic peptides, proteins, peptoids, nucleic acid sequences, including genes, nucleic acid products, and other molecules and compositions. CREB function stimulating agents can be activators of adenylate cyclase 1 (AC1) (e.g., forskolin); cell permeant cAWP analogs (e.g., 8-bromo cAW); agents (neurotransmittors) affecting G-protein linked receptor, such as, but not limited to adrenergic receptors and opioid receptors and their ligands (e.g., isoproterenol, phenethylamines); modulators of intracellular calcium concentration (e.g., potassium chloride, thapsigargin, N-methyl-D-aspartate (NMDA) receptor agonists); inhibitors (antagonists) of the phosphodiesterases responsible for cAMP breakdown (e.g., rolipram (which inhibits phosphodiesterase 4), iso-buto-metho-xanthine (IBMX) (which inhibits phosphodiesterases 1 and 2)); modulators (agonists) of protein kinases and protein phosphatases, which mediate CREB protein activation and CREB-dependent gene expression. CREB function stimulating agents can also be compounds which are capable of enhancing CREB function in the central nervous system (CNS). Such compounds include, but are not limited to, compounds which affect membrane stability and fluidity and specific immunostimulation.

Signaling pathways that activate onto CREB include the mitogen-activated protein kinase (MAPK) signaling pathway and protein kinase A (PKA). Thus, stimulating agents that activate signaling pathways onto CREB include inhibitors of MAPK/Erk kinase (MEK). Other stimulating agents that activate signaling pathways onto CREB are known and readily available to those skilled in the art.

In another embodiment, the primary screen can be replaced with a screening method using *Drosophila*, wherein said screening method comprises: (a) administering a test compound to *Drosophila* having an indicator gene operably linked to a CRE promoter; (b) assessing indicator activity in the *Drosophila* to which have been administered the test compound; and (c) comparing the indicator activity assessed in step (b) with the indicator activity in control *Drosophila* to which have not been administered the test compound. A statistically significant difference in indicator activity in step (b) compared to the indicator activity in control *Drosophila* to which have not been administered the test compound identifies the test compound as a candidate compound.

Host cells comprising an indicator gene operably linked to a CRE promoter can be manufactured by introducing into cells a DNA construct comprising an indicator gene operably linked to a CRE promoter. DNA constructs can be introduced into cells according to methods known in the art (e.g., transformation, direct uptake, calcium phosphate precipitation, electroporation, projectile bombardment, using liposomes). Such methods are described in more detail, for example, in Sambrook et al., Molecular Cloning: A Laboratory Manual, 2nd edition (New York: Cold Spring Harbor University Press) (1989); and Ausubel, et al., Current Protocols in Molecular Biology (New York: John Wiley & Sons) (1998).

*Drosophila* comprising an indicator gene operably linked to a CRE promoter can be produced as described by Belvin et al., Neuron, 22(4):777-787 (1999).

DNA constructs comprising an indicator gene operably linked to a CRE promoter can be manufactured as described in, for example, Ausubel et al., Current Protocols In Molecular Biology (New York: John Wiley & Sons) (1998); and Sambrook et al., Molecular Cloning: A Laboratory Manual, 2nd edition (New York: Cold Spring Harbor University Press (1989).

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. CRE promoters are known in the art.

The term "indicator gene", as used herein, refers to a nucleic acid sequence whose product can be easily assayed, for example, colorimetrically as an enzymatic reaction product, such as the gene encoding luciferase. Other examples of widely used indicator genes include those encoding enzymes, such as $\beta$-galactosidase, $\beta$-glucoronidase and .beta.-glucosidase; luminescent molecules, such as green fluorescent protein and firefly luciferase; and auxotrophic markers such as His3p and Ura3p. See, e.g., Ausubel et al., Current Protocols In Molecular Biology (New York: John Wiley & Sons, Inc.), Chapter 9 (1998)).

Cells (e.g., host cells, cells of neural origin, etc.) contacted with a test compound and/or CREB function stimulating agent will take up the test compound and/or CREB function stimulating agent.

By "suboptimal dose of CREB function stimulating agent" is meant that amount, or dose, of CREB function stimulating agent that is required to stimulate (induce) CREB pathway function to a level that is above endogenous (basal) levels, such that a further statistically significant increase in CREB pathway function due to induction by a cognitive enhancer can be measured and the measurement is not attributable to natural cellular fluctuations or variations as a consequence of natural cellular fluctuations. A suboptimal dose of CREB function stimulating agent is that dose or concentration where the amount of the effect (indicator activity, CREB-dependent gene expression) is proportional to the dose or concentration and the amount of the effect does not change when the dose or concentration changes. The suboptimal dose of CREB function stimulating agent is determined empirically and will vary depending upon a variety of factors, including the pharmacodynamic characteristics of the particular CREB function stimulating agent and the particular cells to be contacted. For example, the suboptimal dose of CREB function stimulating agent can be determined by (a) contacting different samples of a host cell comprising an indicator gene operably linked to a CRE promoter with a different concentration of the CREB function stimulating agent; and (b) determining the range of concentrations of CREB function stimulating agent required to affect indicator activity from baseline to maximal response by assessing indicator activity in the samples of the host cell. The suboptimal dose of CREB function stimulating agent will be any concentration yielding (1) 50% or less maximal indicator activity and (2) an indicator activity above natural cellular fluctuations. Determination of the suboptimal dose of CREB function stimulating agent is well within the ability of those skilled in the art. By "suboptimal dose of a stimulating agent that activates signaling pathways onto CREB" is meant that amount, or dose, of stimulating agent that is required to stimulate (induce) a signaling pathways onto CREB.

By "range of different concentrations of the test compound" is meant 2 or more (i.e., 2, 3, 4, 5, etc.) different concentrations of the test compound. The range of concentrations selected generally flanks the concentration of the test compound in step (a) of the primary screen. By "linear range of (different) concentrations" is meant the concentrations where effect (indicator activity, CREB-dependent gene expression) is increasing with concentration but prior to when the effect is no longer changing with concentration changes. Selecting concentration ranges is well within the ability of those skilled in the art By "functional (biologically active) CREB" is meant to include the protein's DNA binding ability, phosphorylation state, protein stability, subcellular localization, etc.

"CREB-dependent gene expression" is also referred to herein as "CRE-mediated gene expression". CREB-dependent gene expression can be determined by methods known in the art (e.g., Northern blot, Western blot). Such methods are described in more detail, for example, in Ausubel et al., Current Protocols In Molecular Biology (New York: John Wiley & Sons) (1998); and Sambrook et al., Molecular Cloning: A Laboratory Manual, 2nd edition (New York: Cold Spring Harbor University Press (1989).

"Endogenous CRE-mediated genes" are also referred to herein as "endogenous CREB-dependent genes". Such genes are known in the art and include, for example, c-fos, pro-dynorphin, tPA and brain-derived neurotrophic factor (BDNF) (Barco, A. et al., Cell, 108(5):689-703 (2002)). CRE-mediated genes can also be identified by those skilled in the art using methods known and readily available in the art (see, e.g., Ausubel et al., Current Protocols In Molecular Biology (New York: John Wiley & Sons) (1998); and Sambrook et al., Molecular Cloning: A Laboratory Manual, 2nd edition (New York: Cold Spring Harbor University Press (1989)).

The secondary screen comprises: (a) contacting cells of neural origin with a candidate compound identified in the primary screen and with a suboptimal dose of a stimulating agent that activates signaling pathways onto CREB; (b) assessing endogenous CREB-dependent gene expression in the cells which have been contacted with the candidate compound and with the stimulating agent; and (c) comparing endogenous CREB-dependent gene expression assessed in step (b) with endogenous CREB-dependent gene expression in control cells which have been contacted with the stimulating agent and which have not been contacted with the candidate compound (control cells which have been contacted with stimulating agent alone). A statistically significant difference in CREB-dependent gene expression assessed in step (b) compared to the CREB-dependent gene expression in control cells identifies the candidate compound as a confirmed candidate compound. Preferably, no significant difference is obtained in CREB-dependent expression in control cells which have not been contacted with the stimulating agent and which have been contacted with the candidate compound (control cells which have been contacted with candidate compound alone) relative to CREB-dependent gene expression in control cells which have been contacted with neither the stimulating agent or the candidate compound (control cells which have been contacted with nothing). In a particular embodiment, cells are contacted with the candidate compound prior to contact with the stimulating agent.

Alternatively, the secondary screen comprises: (a) contacting cells of neural origin comprising an indicator gene operably linked to a CRE promoter with a candidate compound identified in the primary screen and with a suboptimal dose of a stimulating agent that activates signaling pathways onto CREB; (b) determining indicator activity in the cells which have been contacted with the candidate compound and with the stimulating agent; and (c) comparing indicator activity assessed in step (b) with indicator activity in control cells which have been contacted with the stimulating agent and which have not been contacted with the test compound (control cells which have been contacted with stimulating agent alone). A statistically significant difference in indicator activity determined in step (b) compared to the indicator activity in control cells identifies the candidate compound as a confirmed candidate compound. Preferably, no significant difference is obtained in indicator activity in control cells which have not been contacted with the stimulating agent and which have been contacted with the candidate compound (control cells which have been contacted with candidate compound alone) relative to indicator activity in control cells which have been contacted with neither the stimulating agent or the candidate compound (control cells which have been contacted with nothing). In a particular embodiment, cells are contacted with the candidate compound prior to contact with the stimulating agent.

Preferably, the "stimulating agent that activates signaling pathways onto CREB" used in the primary screen is a CREB function stimulating agent.

In another embodiment, the secondary screen can be replaced with a screening method using Drosophila, wherein said screening method comprises: (a) administering a candidate compound identified in the primary screen to Drosophila having an indicator gene operably linked to a CRE promoter, (b) assessing indicator activity in the Drosophila which have been administered the candidate compound; and (c) comparing the indicator activity assessed in step (b) with the indicator activity in control Drosophila which have not been administered the candidate compound. A statistically significant difference in indicator activity in step (b) compared to the indicator activity in control Drosophila which have not been administered the candidate compound identifies the candidate compound as a confirmed candidate compound.

In a particular embodiment, the cells used in the secondary screen are different from the host cells used in the primary screen. In another embodiment, the endogenous CRE-mediated gene or the CRE-mediated transgene in the secondary screen is different from the CRE-mediated transgene or the endogenous CRE-mediated gene in the primary screen. For example, in one embodiment, the host cells in the primary screen are neuroblastomas and the cells for the secondary screen are not neuroblastomas. In another embodiment, the CRE-mediated transgene in the primary screen is luciferase (CRE operably linked to the luciferase gene) and the CRE-mediated transgene in the secondary screen is not luciferase.

Preferably, the host cells in the primary screen are proliferating cells (such as neuroblastomas) and the cells in the secondary screen are nonproliferating, differentiated cells of neural origin (such as neurons (e.g., primary hippocampal cells) and glial cells). In a particular embodiment, the CRE-mediated gene in the primary screen is a CRE-mediated indicator gene (a CRE-mediated transgene) and the CRE-mediated gene in the secondary screen is an endogenous CRE-mediated gene.

As used herein, a cell refers to an animal cell. The cell can be a stem cell or somatic cell. Suitable animal cells can be of, for example, mammalian origin. Examples of mammalian cells include human (such as HeLa cells), bovine, ovine, porcine, rodent (such as rat, murine (such as embryonic stem cells), rabbit etc.) and monkey (such as COS1 cells) cells. Preferably, the cell is of neural origin (such as a neuroblastoma, neuron, neural stem cell, glial cell, etc.). The cell can also be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions). The cells can be obtained commercially or from a depository or obtained directly from an animal, such as by biopsy.

In one embodiment, the tertiary screen is a behavioral method for assessing long term memory formation in an animal comprising: (a) administering an effective amount of a confirmed candidate compound identified in the secondary screen to the animal (e.g., human, other mammal, vertebrate or invertebrate); (b) training the animal administered the confirmed candidate compound under conditions appropriate to produce long term memory formation in the animal; (c) assessing long term memory formation in the animal trained in step (b); and (d) comparing long term memory formation assessed in step (c) with long term memory formation produced in the control animal to which the confirmed candidate compound has not been administered. If an enhancement is noted in long term memory formation assessed in the animal treated with the confirmed candidate compound relative to the long term memory formation assessed in the control animal the confirmed candidate compound is identified as a cognitive enhancer. Tertiary screens with similar protocols are available using behavioral methods (models) for other, cognitive dysfunctions.

In a particular embodiment, the method for identifying or screening for cognitive enhancers comprise: (a) contacting host cells comprising a luciferase reporter gene operably linked to a CRE promoter with a test compound, thereby producing a test sample; (b) contacting the test sample produced in step (a) with a suboptimal dose of a CREB function stimulating agent (e.g., forskolin, potassium chloride); (c) determining CRE-luciferase activity in the host cells which have been contacted with the test compound and with the CREB function stimulating agent; (d) comparing the CRE-luciferase activity determined in step (c) with the CRE-luciferase activity in control cells which have been contacted with the CREB function stimulating agent and which have not been contacted with the test compound (control cells which have been contacted with CREB function stimulating agent alone); (e) selecting the test compound If it has little or no effect alone and if it further increases CRE-luciferase levels (activity) in host cells which have been contacted with the CREB function stimulating agent, thereby selecting an "Active Hit" compound; (f) repeating steps (a) to (e) using a range of different concentrations of the Active Hit compound selected in step (e); and (g) selecting the Active Hit compound If it has little or no effect alone and if it further proportionally changes the CRE-luciferase levels (activity) in host cells which have been contacted with the CREB function stimulating agent, for the linear range of concentrations of the Active Hit compound, thereby selecting a "Confirmed Active" compound. Host cells comprising a luciferase reporter gene operably linked to a CRE promoter (CRE-driven luciferase reporter gene) can be generated by transfecting the cells with a CRE-driven luciferase reporter gene. Such cells are also referred to herein as CRE-luci cells. In a particular embodiment, the host cells are human neuroblastoma cells. Human neuroblastoma cells transfected with a CRE-driven luciferase reporter gene are also referred to herein as CREluci neuroblastoma cells. A Confirmed Active Hit compound is also referred to herein as a candidate compound.

A Confirmed Active compound (or a candidate compound) can be assessed or evaluated for its effect on endogenous, CRE-mediated gene expression (endogenous CREB-dependent gene expression) by (a) contacting neurons (particularly hippocampal cells) with the Confirmed Active compound (or the candidate compound), thereby producing a sample; (b) contacting the sample with a suboptimal dose of a CREB function stimulating agent; (c) assessing endogenous CREB-dependent gene expression in the neurons which have been contacted with the Confirmed Active compound (or candidate compound) and the CREB function stimulating agent; and (d) comparing endogenous CREB-dependent gene expression assessed in step (c) with endogenous CREB-dependent gene expression in control neurons which have been contacted with the CREB function stimulating agent and which have not been contacted with the Confirmed Active compound (or candidate compound). A statistically significant difference in CREB-dependent gene expression assessed in step (c) compared to the CREB-dependent gene expression in control cells identifies the Confirmed Active compound (or candidate compound) as having an effect on CREB-dependent gene expression and as a confirmed candidate compound. Preferably, no significant difference is obtained in CREB-dependent expression in control cells which have not been contacted with the CREB function stimulating agent and which have been contacted with the Confirmed Active compound (or candidate compound) (control cells which have been contacted with Confirmed Active compound (or candidate compound) alone) relative to CREB-dependent gene expression in control cells which have been contacted with neither the CREB function stimulating agent or the Confirmed Active compound (candidate compound) (control cells which have been contacted with nothing).

The confirmed candidate compound can be assessed or evaluated in an animal (behavioral) model of CREB-dependent long-term memory formation to identify cognitive enhancers. Such methods for assessing or evaluating a confirmed candidate compound to identify cognitive enhancers comprise (a) administering an effective amount of a confirmed candidate compound to an animal; (b) training the animal administered the confirmed candidate compound under conditions appropriate to produce long term memory formation in the animal; (c) assessing long term memory formation in the animal trained in step (b); and (d) comparing long term memory formation assessed in step (c) with long term memory formation produced in the control animal to which the confirmed candidate compound has not been administered. If a statistically significant enhancement is noted in long term memory formation assessed in the animal treated with the confirmed candidate compound relative to the long term memory formation assessed in the control animal, the confirmed candidate compound can be categorized as enhancing (improving, increasing) long term memory formation in the animal and is identified as a cognitive enhancer.

As described herein, confirmed candidate compounds and cognitive enhancers from several chemical classes are progressed through in vivo models of memory formation.

Active compounds are sought that do not enhance CREB pathway function on their own but rather after co-stimulation with a CREB function stimulating agent. This requirement was introduced to mimic results from the original fly experiments: (1) cAMP signaling is involved in the fly memory formation and (2) training is required to enhance memory formation when CREB activator is overexpressed.

Compounds to be evaluated or assessed for their ability to increase CREB pathway function, such as pharmaceutical agents, drugs, chemical compounds, ionic compounds, organic compounds, organic ligands, including cofactors, saccharides, recombinant and synthetic peptides, proteins, peptoids, nucleic acid sequences, including genes, nucleic acid products, and other molecules and compositions, can be individually screened or one or more compound(s) can be tested simultaneously for the ability to increase CREB pathway function in accordance with the methods herein. Where a mixture of compounds is tested, the compounds selected by the methods described can be separated (as appropriate) and identified by suitable methods (e.g., chromatography, sequencing, PCR). The presence of one or more compounds in a test sample having the ability to increase CREB pathway function can also be determined according to these methods. Compounds to be screened for their ability to increase CREB pathway function are generally at a concentration from about 10-9 molar to about 10-3 molar.

Large combinatorial libraries of compounds (e.g., organic compounds, recombinant or synthetic peptides, peptoids, nucleic acids) produced by combinatorial chemical synthesis or other methods can be tested (see e.g., Zuckerman, R. N. et al., J. Med. Chem., 37:2678-2685 (1994) and references cited therein; see also, Ohlineyer, M. H. J. et al., Proc. Natl. Acad. Sci. USA, 90:10922-10926 (1993) and DeWitt, S. H. et al., Proc. Natl, Acad. Sci. USA, 90:6909-6913 (1993), relating to tagged compounds; Rutter, W. J. et at U.S. Pat. No. 5,010,175; Huebner, V. D. et al., U.S. Pat. No. 5,182,366; and Geysen, H. M., U.S. Pat. No. 4,833,092). The teachings of these references are incorporated herein by reference. Where compounds selected from a combinatorial library carry unique tags, identification of individual compounds by chromatographic methods is possible.

Chemical libraries, microbial broths and phage display libraries can also be tested (screened) for the presence of one or more compounds which is capable of enhancing CREB pathway function in accordance with the methods herein.

The invention also relates to methods for assessing the effect of a candidate compound on CREB-dependent gene expression (CRE-mediated gene expression) comprising: (a) contacting cells of neural origin with the candidate compound and with a suboptimal dose of a CREB function stimulating agent; (b) assessing endogenous CREB-dependent gene expression in the cells which have been contacted with the candidate compound and with the CREB function stimulating agent; and (c) comparing endogenous CREB-dependent gene expression assessed in step (b) with endogenous CREB-dependent gene expression in control cells which have been contacted with the CREB function stimulating agent and which have not been contacted with the candidate compound. A statistically significant difference in CREB-dependent gene expression assessed in step (b) compared to the CREB-dependent gene expression in control cells identifies the candidate compound has one having an effect on CREB-dependent gene expression. Preferably, no significant difference is obtained in CREB-dependent expression in control cells which have not been contacted with the CREB function stimulating agent and which have been contacted with the candidate compound relative to CREB-dependent gene expression in control cells which have been contacted with neither the CREB function stimulating agent or the candidate compound (control cells which have been contacted with nothing). In a particular embodiment, cells are contacted with the test compound prior to contact with the CREB function stimulating agent.

Alternatively, methods for assessing the effect of a candidate compound on CREB-dependent gene expression comprise: (a) contacting cells of neural origin comprising an indicator gene operably linked to a CRE promoter with the candidate compound and with a suboptimal dose of a CREB function stimulating agent; (b) determining indicator activity in the cells which have been contacted with the candidate compound and with the CREB function stimulating agent; and (c) comparing indicator activity determined in step (b) with indicator activity in control cells which have been contacted with the CREB function stimulating agent and which have not been contacted with the candidate compound. A statistically significant difference in indicator activity determined in step (b) compared to the indicator activity in control cells identifies the candidate compound has one having an effect on CREB-dependent gene expression. Preferably, no significant difference is obtained in indicator activity in control cells which have not been contacted with the CREB function stimulating agent and which have been contacted with the candidate compound relative to indicator activity in control cells which have been contacted with neither the CREB function stimulating agent or the candidate compound (control cells which have been contacted with nothing). In a particular embodiment, cells are contacted with the test compound prior to contact with the CREB function stimulating agent.

As with the secondary screen, in a particular embodiment, the cells used in the methods for assessing the effect of a candidate compound on CREB-dependent gene expression are different from the host cells in the primary screen. In another embodiment, the endogenous CRE-mediated gene or the CRE-mediated transgene used in the methods for assessing the effect of a candidate compound on CREB-dependent gene expression are different from the CRE-mediated transgene or the endogenous CRE-mediated gene in the primary screen. In another embodiment, the cells used in the methods for assessing the effect of a candidate compound on CREB-dependent gene expression are nonproliferating, differentiated cells of neural origin (such as neurons (e.g., primary hippocampal cells) and glial cells). In a particular embodiment, the CRE-mediated gene in the methods for assessing the effect of a candidate compound on CREB-dependent gene expression is an endogenous CRE-mediated gene.

Enhancement of long term memory formation can be defined as (a) an increase in levels of behavioral performance; (b) a decrease in the number of training trials required to produce a level of behavioral performance; or (c) a decrease in the duration of rest between training sessions to produce a level of behavioral performance. Accordingly, the invention also relates to methods for assessing the effect of a cognitive enhancer on long term memory formation in an animal comprising: (a) administering an effective amount of cognitive enhancer to an animal; (b) training the animal administered the cognitive enhancer under conditions appropriate to produce long term memory formation in said animal; (c) assessing long term memory formation in the animal trained in step (b); and (d) comparing long term memory formation assessed in step (c) with long term memory formation produced in the control animal to which the cognitive enhancer has not been administered. If an enhancement is noted in long term memory formation assessed in the animal treated with the cognitive enhancer relative to the long term memory formation assessed in the control animal, the cognitive enhancer can be categorized as enhancing long term memory formation in the animal. Cognitive enhancers identified as enhancing long term memory formation in the animal are expected to be effective candidates for use in rehabilitating an animal with cognitive dysfunctions and for use in enhancing memory or normal cognitive performance (ability or function) in a normal animal. It is understood that, in certain instances, a cognitive enhancer identified in accordanze with the present invention can be a CREB function stimulating agent Thus, a CREB function stimulating agent may be identified as a cognitive enhancer in accordance with the invention herein.

The phrases "behavior performance" and "cognitive performance" are art-recognized phrases and are used herein in accordance with their art-accepted meaning.

As used herein, the term "animal" includes mammals, as well as other animals, vertebrate and invertebrate (e.g., birds, fish, reptiles, insects (e.g., *Drosophila* species), mollusks (e.g., Aplysia). The terms "mammal" and "mammalian", as used herein, refer to any vertebrate animal, including monotremes, marsupials and placental, that suckle their young and either give birth to living young (eutharian or placental mammals) or are egg-laying (metatharian or non-placental mammals). Examples of mammalian species include humans and primates (e.g., monkeys, chimpanzees), rodents (e.g., rats, mice, guinea pigs) and ruminents (e.g., cows, pigs, horses).

The animal can be an animal with some form and degree of cognitive dysfunction or an animal with normal cognitive performance (i.e., an animal without any form of cognitive failure (dysfunction or loss of any cognitive function)).

An effective amount of cognitive enhancer or confirmed candidate compound is that amount, or dose, administered to an animal that is required to effect a change (increase or decrease) in CREB-dependent gene expression, particularly in cells of neural origin. The dosage administered to an animal, including frequency of administration, will vary depending upon a variety of factors, including pharmacodynamic and pharmacokinetic characteristics of the particular cognitive enhancer or confirmed candidate compound, mode and route of administration; size, age, sex, health, body weight and diet of the recipient; nature and extent of symptoms being treated or nature and extent of the cognitive dysfunction(s) being enhanced or modulated, kind of concurrent treatment, frequency of treatment, and the effect desired.

Training of animals for long term memory formation are conducted using methods generally known in the art (see, e.g., Josselyn et al., Society for Neurosci., 24:926, Abstract 365.10 (1998); Casella and Davis, Physiol. Behav., 36:377-383 (1986); Guzowsli et al., Proc. Natl. Acad. Sci. USA, 94:2693-2698 (1997); Lamprecht et al., J. Neuroscience, 17(21):6443-6450 (1997): Bourtchuladze et al., Cell, 79:59-68 (1994); Kogan et al., Curr. Biol., 7:1-11 (1996); Tully and Quinn, J. Comp. Physiol. A Sens. Neural. Behay. Physiol., 157:263-277 (1985); Tully et al., Cell, 79:35-47 (1994)). Training can comprise one or multiple training sessions. By "multiple training sessions" is meant two or more training sessions.

The invention further relates to methods for assessing the effect of a cognitive enhancer on olfactory memory formation in *Drosophila* comprising: (a) administering an effective amount of cognitive enhancer to *Drosophila*; (b) subjecting the *Drosophila* to classical conditioning and to at least one odorant and electrical shock; and (c) assessing the performance index of the classical conditioning, wherein the effect of the cognitive enhancer occurs when the compound alters the performance index from the performance index obtained by the *Drosophila* of step (a) in the absence of the cognitive enhancer.

The invention also relates to each of the primary, secondary and tertiary screens comprising the methods for identifying or screening for cognitive enhancers described herein.

The invention anticipates a new type of cognitive enhancer that enhances CREB pathway function and augments the therapeutic effects of cognitive training. Such cognitive enhancers can be used as a general therapy for various forms of cognitive dysfunction arising from heredity, disease, injury and age by stimulating the molecular process contributing to brain plasticity and for enhancing memory or normal cognitive performance (ability or function).

Cognitive enhancers identified in accordance with the methods of the invention are compounds with pharmacological activity and include drugs, chemical compounds, ionic compounds, organic compounds, organic ligands, including cofactors, saccharides, recombinant and synthetic peptides, proteins, peptoids, nucleic acid sequences, including genes, nucleic acid products, and other molecules and compositions.

By "modulate" is meant the include the ability to induce, enhance, potentiate, reduce, block, inhibit (total or partial) and regulate a biochemical or physiological action or effect. By "regulate", as the term is used herein, is meant the ability to control the rate and extent to which a process occurs. By "enhance" or "enhancing" is meant the ability to potentiate, increase, improve or make greater or better, relative to normal, a biochemical or physiological action or effect.

Cognitive dysfunction, commonly associated with brain dysfunction and central nervous system (CNS) disorders or conditions, arises due to heredity, disease, injury and/or age. CNS disorders and conditions associated with some form and degree of cognitive failure (dysfunction) include, but are not limited to the following:

1) age-associated or age-dependent memory impairment;

2) mental retardation arising due to a heritable defect, such as, but not limited to that associated with (due to), chromosomal abnormalities, including Rubinstein-Taybi syndrome, down syndrome, fragile X syndrome, cri du chat syndrome, Klinefelter's syndrome, Turner's syndrome, mosaicisms, Patau's syndrome (trisomy 13) and Edward's syndrome (trisomy 18); genetic metabolic abnormalities, including Coffin-Lowry syndrome, autosomal recessive disorders, such as aminoacidurias and acidemias, peroxisomal disorders, such as galactosemia, maple syrup urine disease and phenylketonuria, lysosomal defects, such as Gaucher's disease, Hurler's syndrome (mucopolysaccharidosis), Niemann-Pick disease and Tay-Sachs disease, and X-linked recessive disorders, such as Lesch-Nyhan syndrome (hyperuricemia), Hunter's syndrome (a variant of mucopolysaccharidosis) and Lowe's oculocerebrorenal syndrome; genetic neurological abnormalities, including autosomal dominant disorders, such as myotonic dystrophy, neurofibromatosis and tuberous sclerosis, and autosomal recessive disorders, such as primary microcephaly, 3) trauma-dependent loss of cognitive function, such as, but not limited to that associated with (due to), cerebrovascular diseases, including stroke and ischemia, including ischemic stroke; brain trauma, including subdural hematoma and brain tumor; head injury;

4) neurodegenerative disorders, such as delirium (acute confusional state); dementia, including Alzheimer's disease and non-Alzheimer's type dementias, such as, but not limited to, Lewy body dementia, vascular dementia, Binswanger's dementia (subcortical arteriosclerotic encephalopathy), dementias associated with Parkinson's disease, progressive supranuclear palsy, Huntington's disease (chorea), Pick's disease, normal-pressure hydrocephalus, Creutzfeldt-Jakob disease, Gerstmann-Straussler-Scheinker disease, neurosyphilis (general paresis) or HIV infection, frontal lobe dementia syndromes, dementias associated with head trauma, including dementia pugilistica, brain trauma, subdural hematoma, brain tumor, hypothyroidism, vitamin B.sub.12 deficiency intracranial radiation; other neurodegenerative diseases and disorders;

5) psychiatric disorders, including affective disorders (mood disorders), such as, but not limited to, depression, including depressive pseudodementia; psychotic disorders, such as, but not limited to, schizophrenia and autism (Kanner's Syndrome); neurotic disorders, such as, but not limited to, anxiety and obsessive-compulsive disorder; attention deficit disorder; and 6) learning, language or reading disabilities, particularly in children. By "learning disabilities" is meant disorders of the basic psychological processes that affect the way an individual learns. Learning disabilities can cause difficulties in listening, thinking, talking, reading, writing, spelling, arithmetic or combinations of any of the foregoing. Learning disabilities include perceptual handicaps, dyslexia and developmental aphasia.

Cognitive enhancers and confirmed candidate compounds can be administered directly to an animal in a variety of ways. In a preferred embodiment, cognitive enhancers and confirmed candidate compounds are administered systemically. Other routes of administration are generally known in the art and include intravenous including infusion and/or bolus injection, intracerebroventricularly, intrathecal, parenteral, mucosal, implant, intraperitoneal, oral, intradermal, transdermal (e.g., in slow release polymers), intramuscular, subcutaneous, topical, epidural, etc. routes. Other suitable routes of administration can also be used, for example, to achieve absorption through epithelial or mucocutaneous linings. Particular cognitive enhancers and confirmed candidate compounds can also be administered by gene therapy, wherein a DNA molecule encoding a particular therapeutic protein or peptide is administered to the animal, e.g., via a vector, which causes the particular protein or peptide to be expressed and secreted at therapeutic levels in vivo.

A vector, as the term is used herein, refers to a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

The mode of administration is preferably at the location of the target cells. In a particular embodiment, the mode of administration is to cells of neural origin Cells of neural origin include neural stem cells, neuroblastoma cells, neurons and glial cells.

Cognitive enhancers and confirmed candidate compounds can be administered together with other components of biologically active agents, such as pharmaceutically acceptable surfactants (e.g., glycerides), excipients (e.g., lactose), stabilizers, preservatives, humectants, emollients, antioxidants, carriers, diluents and vehicles. If desired, certain sweetening, flavoring and/or coloring agents can also be added.

Cognitive enhancers and confirmed candidate compounds can be formulated as a solution, suspension, emulsion or lyophilized powder in association with a pharmaceutically acceptable parenteral vehicle. Examples of such vehicles are water, saline, Ringer's solution, isotonic sodium chloride solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation can be sterilized by commonly used techniques. Suitable pharmaceutical carriers are described in Remington's Pharmaceutical Sciences.

Cognitive enhancers and confirmed candidate compounds can be administered in single or divided doses (e.g., a series of doses separated by intervals of days, weeks or months), or in a sustained release form, depending upon factors such as nature and extent of symptoms, kind of concurrent treatment and the effect desired. Other therapeutic regimens or agents can be used in conjunction with the present invention.

The present invention will now be illustrated by the following example, which is not to be considered limiting in any way.

EXAMPLES

Example 1

From the drug discovery program described herein, lead compounds from several chemical classes are progressed through in vivo models of memory formation.

Drug Discovery

Two basic principles guide the drug discovery program. First, active compounds are sought that do not enhance CREB function on their own but rather after co-stimulation with forskolin, an activator of adenylyl cyclase. This requirement was introduced to mimic results from the original *Drosophila* experiments: (1) cAMP signaling is involved in the fly memory formation and (2) training is required to enhance memory formation when CREB activator is overexpressed. Second, CREB appears to function similarly in neurons from various vertebrate and invertebrate species. To capitalize on this evolutionary conservation, a drug progression pathway was developed that includes fly, rodent and human assays.

Primary Screen

A cell-based, high throughput screen (HTS) was designed to assess the effects of compounds on CREB pathway function. Human neuroblastoma cells (SKN-MC) were transfected stably with a reporter construct, in which luciferase was placed under the control of a CRE promoter. With this reporter, increases in CREB pathway function were monitored via fluorescent output. This tester cell line was evaluated fully using known CREB activators.

To assess compound activity, the tester line was pre-incubated in the presence of compound and then was stimulated with a suboptimal dose of forskolin prior to lysis. The concentration and time-course for forskolin co-stimulation were calibrated to reproducibly obtain 30% saturation, yielding a 300% range for compound effects. Compounds that produced ≥100% increase in luciferase signal over control cells stimulated with forskolin alone were progressed to a second round of screening to exclude statistical false positives. Finally, these compounds were assessed at four different concentrations with or without forskolin co-stimulation. To date, 155,000 compounds have been screened with this approach, yielding about 180 Confirmed Actives.

Secondary Screens

Eighty six of the 180 Confirmed Actives were chosen for further analysis based on their structure and potency. To rule out any potential artifactual effects of the reporter gene construct, real time quantitative PCR (QPCR) was used to assess expression levels of known, endogenous CREB-dependent genes in the tester line. Most of the confirmed actives showed comparable potency profiles for both luciferase reporter gene expression and endogenous gene expression. Structural analyses of these 86 Confirmed Actives revealed 10 to be digitoxigenin related, 26 to be phenylethylamine derivatives, 4 to be aminopropanediol derivatives, 3 to be phosphodiesterase inhibitors and 3 to be caffeine analogues. The remaining 40 were novel chemical structures with no obvious similarities to other known compounds. Of these, 11 Active Hits were chosen for further study based on potency, solubility and ease to derivatize. For these 11 Active Hits, enhancement of endogenous CREB-dependent gene expression was confirmed in cultured rat primary hippocampal neurons. Functional (enzymatic, binding affinity, etc.) analyses revealed 8 to be PDE IV inhibitors and 2 to target other molecules.

In Vivo Assays

The 11 Active Hits were fed to transgenic flies, carrying a CRE-luciferase transgene. Previous experiments had established that: (1) reporter gene activity could be quantified from single flies and (2) the CRE-luciferase reporter normally showed a circadian cycle of expression (Belvin, M. P. et al., Neuron, 22(4):777-787 (1999)). These observations revealed an efficient initial in vivo assay with which to determine the drug concentrations needed to affect CRE-luciferase expression in brain tissue of drug-fed flies. All 11 Lead Candidates produced a significant increase in CRE-luciferase expression levels in vivo. One of these compounds was tested in vivo for its effects on fly olfactory memory formation. It showed a partial enhancement of memory after massed training and no effect on memory after spaced training—a result reminiscent of the CREB signature.

These Active Hits were evaluated in vivo rodent models of memory formation. To do so efficiently, a new behavioral training protocol was validated, which logically was affected by upstream modulation of the CREB pathway. During initial stages of acquisition, repeated training trials lead to increased cAMP levels. At some point, cAMP levels pass a threshold, and activated PKA (catalytic subunit) is translocated to the nucleus, where it phosphorylates CREB directly or it yields a permissive state for the phosphorylation of CREB by a cofactor. In this context, phosphodiesterase (PDE) inhibitors act to increase cAMP levels beyond the threshold with fewer training trials, thereby producing more long-lasting memory with weaker training. Using the prototypical PDE inhibitor, rolipram, this effect was established as predicted (FIG. 1).

Taken together these data indicate that PDE is an efficacious drug target to enhance CREB function.

Example 2

Method for Identifying Functional CREB Antisense Oligos

Detection of CREB mRNA with the bDNA Assay. *Mus musculus* Neuro2a cells were obtained from American Type Culture Collection (ATCC, Cat. No. CCL-131; Manassas, Va.). Cells were plated in Modified Eagle's Minimum Essential Media (Minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate, 90%; fetal bovine serum, 100%) in a 96-microwell format at $2 \times 10^4$ cells per well. Cells were maintained at 37 C. and 5% CO2 overnight before transfecting with CREB Locked Nucleic Acid (LNA) oligonucleotides.

Cells were transfected using Lipofectamine 2000 (hivitrogen, Carlsbad, Calif.) with modifications to the manufacturer's protocol. For each transfection sample, the corresponding CREB LNA oligonucleotide (see sequences below) was diluted with 25 μl Opti-MEM reduced-serum media (HEPES buffer, 2,400 mg/L sodium bicarbonate, hypoxanthine, thyrmidine, sodium pyruvate, L-glutamine, trace elements, growth factors, and phenol red reduced to 1.1 mg/L (Invitrogen) to a final transfection concentration of 0.2 μM. The Lipofectamine 2000 was also diluted in 25 μ.1 Opti-MEM reduced-serum media so the ratio of LNA oligonucleotide (μl) to Lipofectamine 2000 (μl) was 1:3, respectively. The diluted LNA oligonucleotide was combined with the diluted Lipofectamine 2000 and incubated for 15 minutes at room temperature for the complexes to form. Fifty μl of LNA oligonucleotide-Lipofectamine 2000 complexes were added to each well. Transfections were performed in triplicate for each CREB LNA oligonucleotide at 0.2 μM. The cells were incubated at 37 C. and 5% CO.2 for 24 hours. Growth medium was replaced after 5 hours with 100 μMEME medium.

The direct quantitation of CREB messenger RNA (mRNA) following transfection of antisense oligos, was detected using the QuantiGene Expression Kit according to the manufacturer's protocol (Bayer Corporation; Tarrytown, N.Y.). Twenty four hours post antisense LNA oligonucleotide transfections, the cells were lysed with 50 .mu.l lysis buffer (Bayer Corporation) containing the pooled CREB specific Capture Extenders (CE), Label Extenders (LE), and blocking (BL) oligonucleotides (described below). After a 30 minute incubation, 100 μl of the lysis mixture from each well were added to a corresponding capture well (Bayer Corporation). The capture plate was sealed with an adhesive-backed Plate Sealer (Bayer Corporation) and incubated overnight at 50 C. The wells were washed three times with 390 μl of wash buffer (0.1×SSC and 0.03% Lithium Lauryl Sulfate) in an ELx405 Plate Washer (BioTek Instruments). 100 .mu.1 of amplifier reagent containing amplifier probe diluted 1:1000 in amplifier/label probe diluent (provided by Bayer Corporation) was immediately added to each well of the capture plate, sealed, and incubated at 50 C. for 60 minutes. The wells were washed three times with wash buffer as described above and 100 μl of labeling reagent containing label probe diluted 1:1000 in amplifier/label probe diluent (Bayer Corporation) was immediately added to each well of the capture plate. The capture plate was sealed and incubated at 50 C. for 60 minutes. The wells were washed three times with wash buffer as described above and 100 μl of substrate working solution (0.003% Lithium Lauryl Sulfate in Substrate Working Reagent; Bayer Corporation) was immediately added to each well of the capture plate. The capture plate was sealed and incubated at 50 C. for 30 minutes. The luminescence of each well was measured in a Wallac Victor2 V (Perkin Elmer) plate luminometer at 45 C.

Figure 3:
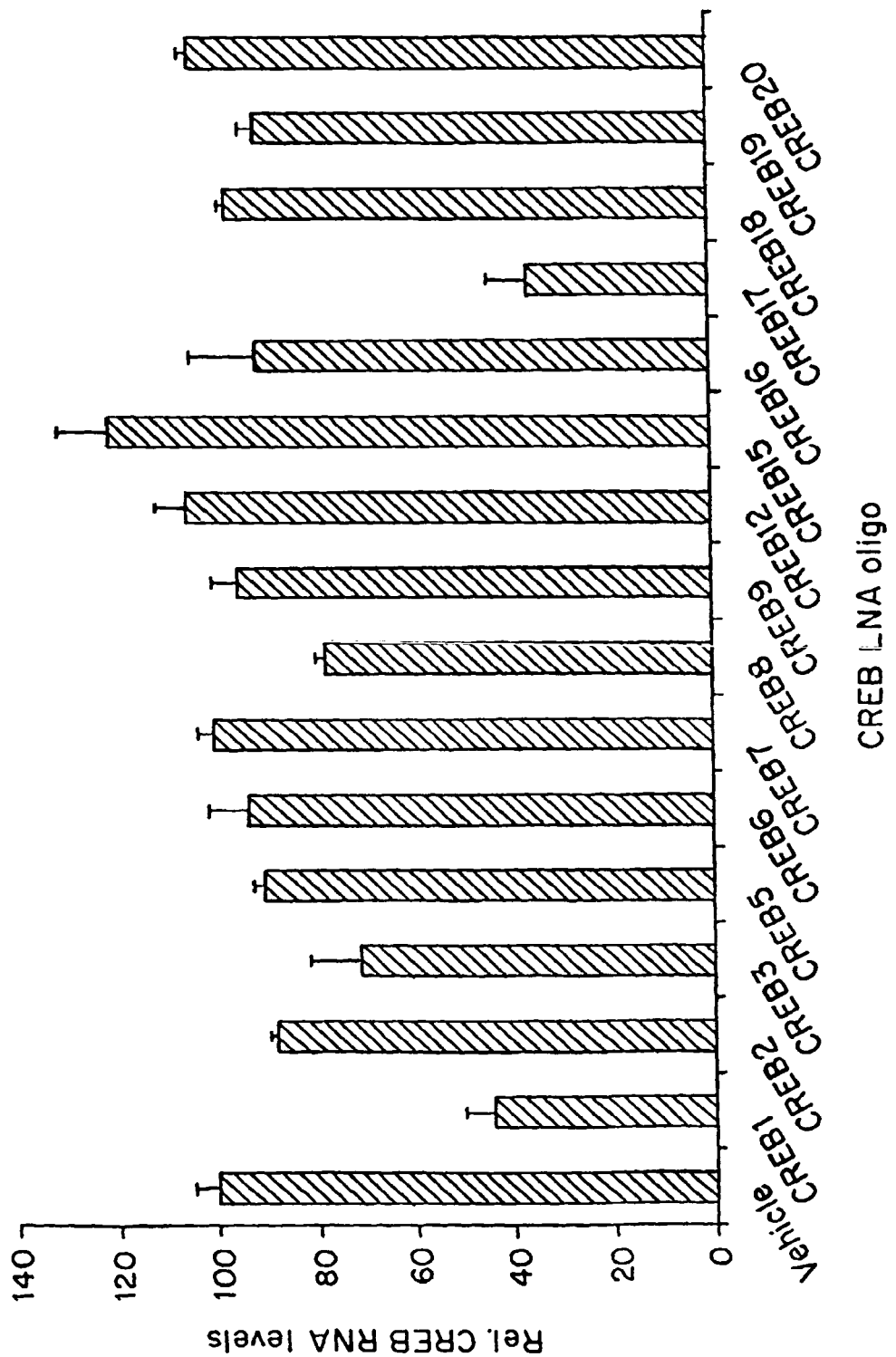
FIG. 3 is a bar graph showing the results of a CREB Locked Nucleic Acid (LNA) antisense screen. The CREB LNB oligos are numbered in the order that they were designed. CREB LNB oligos that were not screened (i.e., CREB 4, 10, 11, 13 and 14) are not shown.

FIG. 3 shows the effects of various different CREB antisense LNA oligos on levels of CREB RNA in Neuro2a 131 cells following transfection, relative to cells treated with vehicle control (transfection reagent minus any oligo). Each CREB LNA oligo has a unique sequence (see below). The CREB LNB oligos were numbered in the order that they were designed. CREB LNB oligos that were not screened (tested) because they did not have suitable properties (e.g., melting temperature) when analyzed (i.e., CREB 4, 10, 11, 13 and 14) are not shown. The results demonstrate that oligos CREB1 and CREB17 reduce endogenous CREB RNA levels by at least 50%.

Oligo CREB3 is a sequence that has previously been used to knock down CREB RNA (as a phosphorothioate oligo). The results herein demonstrate that oligo CREB3 also reduces endogenous CREB RNA levels, although at a higher concentration (0.5 μM).

CREB Locked Nucleic Acid Oligonucleotide Design. Antisense oligonucleotides were designed for CREB using the sequence for GenBank Accession Number M95106 with Vector NTI Suite 8 (InforMax, Frederick, Md.). The sequences of the Locked Nucleic Acid (LNA) oligonucleotides (Proligo LLC, Boulder, Colo.) are summarized below:

| | | |
|---|---|---|
| 1. | CCTCCgCCgCgTCACTCA | (SEQ ID NO. 1) |
| 2. | CCACgTAACACACCgCgT | (SEQ ID NO.: 2) |
| 3. | TggTCATTTAgTTACCggTg | (SEQ ID NO.: 3) |
| 4. | gCTggTTgTCTgCACCAG | (SEQ ID NO.: 4) |
| 5. | TTTTCAgCTTCTgTTACA | (SEQ ID NO. 5) |
| 6. | CTgggCTTgAACTgTCAT | (SEQ ID NO.: 6) |
| 7. | gCTAATgTggCAATCTgT | (SEQ ID NO.: 7) |
| 8. | TgCTggCATggATACCTg | (SEQ ID NO.: 8) |
| 9. | gCAgATgATgTTgCATgA | (SEQ ID NO.: 9) |
| 10. | TgTCTgCCCATTgggCAg | (SEQ ID NO.: 10) |
| 11. | gggCCgCCTggATAACgCC | (SEQ ID NO.: 11) |
| 12. | TTCACTTTCTgCAATAgT | (SEQ ID NO.: 12) |
| 13. | TCCACAgACTCCTgTgAA | (SEQ ID NO.: 13) |
| 14. | AAAggATTTCCCTTCgTT | (SEQ ID NO.: 14) |
| 15. | CAgAAgATAAgTCATTCA | (SEQ ID NO.: 15) |
| 6. | TTCTCAATCCTTggCAC | (SEQ ID NO.: 16) |
| 7. | TggCACTgTTACAgTggT | (SEQ ID NO.: 17) |
| 18. | CTgCCCACTgCTAgTTTg | (SEQ ID NO.: 18) |
| 19. | gCTCCTCCgTCACTgCTT | (SEQ ID NO.: 19) |
| 20. | TgCACTAAggTTACAgTg. | (SEQ ID NO.: 20) |

Individual LNA oligonucleotides were resuspended in 1×TE (10 mM Tris HCl, pH 8.0 and 1 mM EDTA, pH 8.0) at a concentration of 200 μM.

CREB bDNA Probe Design.

Oligonucleotide probes were designed for the capture and signal amplification of the CREB mRNA with QuantiGene ProbeDesigner Software (Bayer Corporation). The sequences of oligonucleotides (Integrated DNA Technologies Inc; Coralville, Iowa) are summarized below:

(SEQ ID NO.: 21)
CE ggatttcccttcgtttttgggTTTTTctcttggaaagaaagt (SEQ ID NO.: 22)
CE caatccttggcaccctggtTTTTTctcttggaaagaaagt (SEQ ID NO.: 23)
CE agtctcctcttctgacttttcttcttTTTTTctcttggaaagaaagt (SEQ ID NO.: 24)
CE tcctccctgggtaatggcaTTTTTctcttggaaagaaagt (SEQ ID NO.: 25)
CE ccattgttagccagctgtattgcTTTTTctcttggaaagaaagt (SEQ ID NO.: 26)
CE ccggctgagtggcagctgTTTTTctcttggaaagaaagt (SEQ ID NO.: 27)
CE gcctgaggcagcttgaacaTTTTTctcttggaaagaaagt (SEQ ID NO.: 28)
CE tgctgcttcttcagcaggctTTTTTctcttggaaagaaagt (SEQ ID NO.: 29)
CE ttagacggacctctctcttccgTTTTTctcttggaaagaaagt (SEQ ID NO.: 30)
LE gaatcttcactttctgcaatagttgaTTTTTaggcataggacccgtgtct (SEQ ID NO.: 31)
LE aatcagttacactatccacagactcctgtTTTTTaggcataggacccgtgtct (SEQ ID NO.: 32)
LE atgtactgcccactgctagtttggtaTTTTTaggcataggacccgtgtct (SEQ ID NO.: 33)
LE ggccctgtacccatccgtaTTTTTaggcataggacccgtgtct (SEQ ID NO.: 34)
LE cattggtcatggttaatgtctgcaTTTTTaggcataggacccgtgtct (SEQ ID NO.: 35)
LE gtctgtgcatactgtagaatggtagtacTTTTTaggcataggacccgtgtct (SEQ ID NO.: 36)
LE agaatctgctgtccatccgtgTTTTTaggcataggacccgtgtct (SEQ ID NO.: 37)
LE gtgcgaatctggtatgtttgtacatcTTTTTaggcataggacccgtgtct (SEQ ID NO.: 38)
LE acgccataacaactccagggTTTTTaggcataggacccgtgtct (SEQ ID NO.: 39)
BL cctgtaggaaggcctccttgaaa (SEQ ID NO.: 40)
BL gcatcagaagataatcattcaaaatttt (SEQ ID NO.: 41)
BL tggtgatggcaggggctga (SEQ ID NO.: 42)
BL aatgggggttggcactgttacag -continued BL acaacttggttgctgggcact (SEQ ID NO.: 43)

BL gcaatggtgctagtgggtgct (SEQ ID NO.: 44)

BL gtgtaggaagtgctggggagg (SEQ ID NO.: 45)

Individual (CE), (LE), and (BL) probes were resuspended in 1×TE, pH 8.0 at a concentration of 100 pmoles/µl. The target specific (CE), (LE), and (BL) probe set pools were resuspended in 1×TE at a final concentration of 50, 200, and 100 fmol/µl, respectively.

Effect of CREB Antisense LNA oligos on CRE-Luci Response to Forskolin+HT0712 in SK-N-MC Cells.

Human SK-N-MC cells (see Example 1), stably transfected with a reporter construct consisting of the VIP promoter containing 2 CRE elements together with 2 additional CRE elements from the tyrosine aminotransferase gene driving expression of luciferase, were plated in Iscoves Modified Eagle's Medium (IMEM, Invitrogen, Carlsbad, Calif.), with 2 mM L-glutamine, 0.1 mM Non-essential amino acids, 0.1 mM HEPES, 10% fetal bovine serum at a density of 20,000 cells per well in a 96 well plate format. Cells were maintained at 37 C., 5% $CO_2$ overnight before transfection with 0.2 µM CREB LNA antisense oligonucleotides. Functional CREB oligos were identified in the bDNA screen described earlier. CREB LNA oligos utilized were:

```
CREB 1:   CCTCCgCCgCgTCACTCA  (SEQ ID NO.: 46)
CREB 3:   CCACgTAACACACCgCgT  (SEQ ID NO.: 47)
CREB 17:  TggCACTgTTACAgTggT  (SEQ ID NO.: 48)
```

CREB 1 and CREB 3 oligos have identical sequence homology with both mouse and human. CREB 17 has a single base mismatch. All three LNA oligos have been shown to be factional in knocking down human CREB RNA levels in a human CREB bDNA assay.

Cells were transfected with human CREB LNA oligos using Lipofectamine 2000 (Invitrogen, Carlsbad, Calif.) with modifications to the manufacturer's protocol. For each transfection sample, the corresponding CREB LNA oligonucleotide (CREB oligos 1, 3 and 17) was diluted with 25 µl Opti-MEM reduced-serum media (HEPES buffer, 2,400 mg/L sodium bicarbonate, hypoxanthine, thymidine, sodium pyruvate, L-glutamine, trace elements, growth factors, and phenol red reduced to 1.1 mg/L; Invitrogen) to a final transfection concentration of 0.2 µM. The Lipofectamine 2000 was also diluted in 25 µl Opti-MEM reduced-serum media so the ratio of LNA oligonucleotide (µl) to Lipofectamine 2000 (µl) was 1:3, respectively. The diluted LNA oligonucleotide was combined with the diluted Lipofectamine 2000 and incubated for 15 minutes at room temperature for the complexes to form. 50 µl of LNA oligonucleotide-Lipofectamine 2000 complexes were added to each well. The cells were incubated at 37 C. and 5% CO2 for 16-24 hours. Growth medium was replaced after 5 hours with 100 µl IMEM medium.

5 µM HT0712 ((3S,5S)-5-(3-cyclopentyloxy-4-methoxyphenyl)-3-(3-ethyl-benzyl)-piperidin-2-one; also known as IPL 455,903)) was added to the transfected/vehicle treated cells, and incubated at 37 C, 5% CO2 for 2 hours. HT0712 has the following formula:

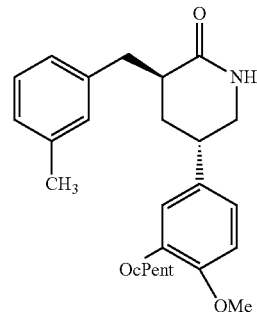

wherein "Me" means "methyl" and "cPent" means "cyclopentyl". HT0712 can be prepared using the methodology provided in U.S. Pat. No. 6,458,829 B1, the teachings of which are incorporated herein by reference.

2 µM forskolin was then added, and the cells incubated for a further 6 hours, washed briefly with PBS, lysed in the presence of luciferin and luciferase activity measured using a Victor 5 luminometer.

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
   1) screening a plurality of compounds for potential development as-candidate cognitive enhancer compounds by
   2) determining the ability of said compounds to enhance cyclic adenosine monophosphate (cAMP) response element binding protein (CREB) pathway function wherein said screening and determining comprises the steps of:
      a) contacting cells of neural origin comprising an indicator gene operably linked to a cAMP response element (CRE) promoter with a test compound and with a suboptimal dose of a CREB function stimulating agent simultaneously or sequentially, wherein said CREB function stimulating agent is forskolin;
      b) determining indicator activity in said cells of neural origin which have been contacted with said test compound and with said CREB function stimulating agent, wherein said CREB function stimulating agent is forskolin;
      c) determining indicator activity in said cells of neural origin which have been contacted with said CREB function stimulating agent alone, wherein said CREB function stimulating agent is forskolin;
      d) determining indicator activity in said cells of neural origin which have been contacted with said test compound alone; and
      e) determining indicator activity in said cells of neural origin which have not been contacted with said test compound or said CREB function stimulating agent, wherein said CREB function stimulating agent is forskolin;
      f) comparing the indicator activity determined in each of steps b) through e)
      g) selecting said test compound if:
         i) the indicator activity determined in step b) is significantly increased relative to the indicator activity determined in step c); and
         ii) the indicator activity determined in step d) is not significantly different relative to the indicator activity determined in step e);
      h) repeating steps a) to g) with a range of different concentrations of said test compound selected in step g); and
      i) selecting said test compound if:
         i) the indicator activity determined in step b) is significantly increased relative to the indicator activity determined in step c); and
         ii) the indicator activity determined in step d) is not significantly different relative to the indicator activity determined in step e) in the range of different concentrations of said test compound, and
   3) identifying said test compound as a candidate cognitive enhancer compound if said test compound is selected in steps g) and i).

2. The method of claim 1 wherein said cells of neural origin are contacted with said test compound prior to contact with said CREB function stimulating agent.

3. The method of claim 1 wherein said cells of neural origin are human neuroblastoma cells.

4. The method of claim 1 wherein said indicator gene encodes luciferase.

5. The method of claim 1 wherein steps a) to g) are repeated with a range of at least four different concentrations of the said test compound selected in step g).

6. The method of claim 1 wherein said cells of neural origin are contacted with said candidate cognitive enhancer compound prior to contact with said CREB function stimulating agent, wherein said CREB function stimulating agent is forskolin.

7. The method of claim 1 wherein said cells of neural origin are neurons.

8. The method of claim 7 wherein said neurons are primary hippocampal cells.

9. A method comprising:
   1) screening a plurality of compounds for potential development as candidate cognitive enhancer compounds by
   2) determining the ability of said compounds to enhance cyclic adenosine monophosphate (cAMP) response element binding protein (CREB) pathway function wherein said screening and determining comprises the steps of:
      a) contacting host cells comprising an indicator gene operably linked to a cAMP response element (CRE) promoter with a test compound and with a suboptimal dose of a CREB function stimulating agent simultaneously or sequentially, wherein said CREB function stimulating agent is forskolin;
      b) determining indicator activity in said host cells which have been contacted with said test compound and with said CREB function stimulating agent, wherein said CREB function stimulating agent is forskolin;
      c) determining indicator activity in said host cells which have been contacted with said CREB function stimulating agent alone, wherein said CREB function stimulating agent is forskolin;
      d) determining indicator activity in said host cells which have been contacted with said test compound alone; and
      e) determining indicator activity in said host cells which have not been contacted with said test compound or said CREB function stimulating agent, wherein said CREB function stimulating agent is forskolin;
      f) comparing the indicator activity determined in each of steps b) through e)
      g) selecting said test compound if:
         i) the indicator activity determined in step b) is increased >100% relative to the indicator activity determined in step c); and
         ii) the indicator activity determined in step d) is not significantly different relative to the indicator activity determined in step e); and
      h) repeating steps a) to g) with a range of different concentrations of said test compound selected in step g); and
      i) selecting said test compound if:

i) the indicator activity determined in step b) is significantly increased relative to the indicator activity determined in step c); and ii) the indicator activity determined in step d) is not significantly different relative to the indicator activity determined in step e) in the range of different concentrations of said test compound, and 3) identifying said test compound as a candidate cognitive enhancer compound if said test compound is selected in steps g) and i).

10. The method of claim 9 wherein said host cells are contacted with said test compound prior to contact with said CREB function stimulating agent.

11. The method of claim 9 wherein said indicator gene encodes luciferase.

12. The method of claim 9 wherein steps a) to g) are repeated with a range of at least four different concentrations of the said test compound selected in step g).

13. The method of claim 9 wherein said host cells are cell of neural origin.

\* \* \* \* \*